United States Patent
Holladay et al.

(10) Patent No.: US 6,274,587 B1
(45) Date of Patent: Aug. 14, 2001

(54) TRICYCLIC DIHYDROPYRIMIDINE POTASSIUM CHANNEL OPENERS

(75) Inventors: Mark W. Holladay, Tucson, AZ (US); William A. Carroll, Evanston, IL (US); Irene Drizin, Wadsworth, IL (US); Lin Yi, Gurnee, IL (US); Henry Q. Zhang, Grayslake, IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 09/443,212

(22) Filed: Nov. 19, 1999

(51) Int. Cl.⁷ .................... C07D 239/70; C07D 471/14; A61K 31/517; A61K 31/519; A61P 15/10
(52) U.S. Cl. .................... 514/267; 544/250; 544/251; 544/252
(58) Field of Search .................... 544/250, 251, 544/252; 514/267

(56) References Cited

U.S. PATENT DOCUMENTS 4,918,074  4/1990  Tsuda et al. .................... 514/258

FOREIGN PATENT DOCUMENTS

| 0183848 | 6/1986 | (EP) . |
| 0217142 | 4/1987 | (EP) . |
| 0328700 | 8/1989 | (EP) . |
| 227584 | 10/1986 | (JP) . |
| 6360985 | 3/1988 | (JP) . |
| 243029 | 10/1988 | (JP) . |
| 02188747 | * 7/1990 | (JP) . |
| 8504172 | 3/1984 | (WO) . |

OTHER PUBLICATIONS

Atwal & Moreland, "Dihydropyrimidine Calcium Channel Blockers 51: Bicyclic Dihydropyrimidines as Potent Mimics of Dihydropyridines" *Bioorganic & Medicinal Chemistry Letters,* 1(6):291–294 (1991).

* cited by examiner

*Primary Examiner*—Mukund J. Shah
*Assistant Examiner*—Hong Liu
(74) *Attorney, Agent, or Firm*—Michael J. Ward

(57) ABSTRACT

Compounds of formula I

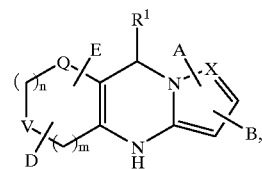

are useful in treating diseases prevented by or ameliorated with potassium channel openers. Also disclosed are potassium channel opening compositions and a method of opening potassium channels in a mammal.

57 Claims, No Drawings

TRICYCLIC DIHYDROPYRIMIDINE POTASSIUM CHANNEL OPENERS

TECHNICAL FIELD

Novel tricyclic dihydropyrimidine compounds and their derivatives can open potassium channels and are useful for treating a variety of medical conditions.

BACKGROUND OF INVENTION

Potassium channels play an important role in regulating cell membrane excitability. When the potassium channels open, changes in the electrical potential across the cell membrane occur and result in a more polarized state. A number of diseases or conditions may be treated with therapeutic agents that open potassium channels; see (K. Lawson, Pharmacol. Ther., v. 70, pp. 39–63 (1996)); (D. R. Gehlert et al., Prog. Neuro-Psychopharmacol & Biol. Psychiat., v. 18, pp. 1093–1102 (1994)); (M. Gopalakrishnan et al., Drug Development Research, v. 28, pp. 95–127 (1993)); (J. E. Freedman et al., The Neuroscientist, v. 2, pp. 145–152 (1996)); (D. E. Nurse et al., Br. J. Urol., v. 68 pp. 27–31 (1991)); (B. B. Howe et al., J. Pharmacol. Exp. Ther., v. 274 pp. 884–890 (1995)); and (D. Spanswick et al., Nature, v. 390 pp. 521–25 (Dec. 4, 1997)). Such diseases or conditions include asthma, epilepsy, hypertension, male sexual dysfimction, female sexual dysfunction, migraine, pain, urinary incontinence, stroke, Raynaud's Syndrome, eating disorders, finctional bowel disorders, and neurodegeneration.

Potassium channel openers also act as smooth muscle relaxants. Because urinary incontinence can result from the spontaneous, uncontrolled contractions of the smooth muscle of the bladder, the ability of potassium channel openers to hyperpolarize bladder cells and relax bladder smooth muscle provides a method to ameliorate or prevent urinary incontinence.

U.S. Pat. No. 4,918,074, EP 183848 B1, EP 217142, EP 328700, JP 63060985, JP 63243029, JP 61227584, and Atwal, K.S., Bioorg. Med. Chem. Lett (1991) 1, 291–294 disclose bicyclic 4,7-dihydropyrazolo[1,5-a]pyrimidines.

The compounds of the present invention are novel, hyperpolarize cell membranes, open potassium channels, relax smooth muscle cells, inhibit bladder contractions, and are useful for treating diseases that can be ameliorated by opening potassium channels.

SUMMARY OF THE INVENTION

In its principle embodiment, the present invention discloses compounds of formula I:

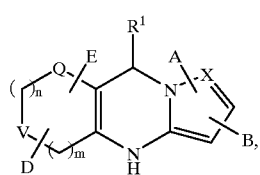

I or a pharmaceutically acceptable salt, ester, amide, or prodrug thereof wherein, n is an integer 0–1;

m is an integer 1–2;

provided that when m is 2, n is 0;

$R^1$ is selected from aryl and heterocycle;

Q is selected from C(O), S(O), and $S(O)_2$;

V is selected from $C(R^6)(R^7)$, O, S, and $NR^2$, wherein $R^2$ is selected from hydrogen, alkenyl, alkoxy, alkoxyalkoxy, alkoxyalkyl, alkyl, alkynyl, aryl, arylalkoxy, arylalkenyl, arylalkyl, cyano, cycloalkyl, cycloalkylalkyl, haloalkoxy, haloalkyl, heterocycle, heterocyclealkyl, hydroxy, hydroxyalkyl, $—NR^4R^5$, and $(NR^4R^5)$alkyl wherein $R^4$ and $R^5$ are independently selected from hydrogen and lower alkyl;

$R^6$ and $R^7$ are independently selected from hydrogen, alkenyl, alkoxy, alkoxyalkoxy, alkoxyalkyl, alkyl, alkylthio, alkynyl, aryl, arylalkoxy, arylalkenyl, arylalkyl, carboxy, cyano, cycloalkyl, cycloalkylalkyl, haloalkoxy, haloalkyl, halogen, heterocycle, heterocyclealkyl, hydroxy, hydroxyalkyl, oxo, $—NR^4R^5$, and $(NR^4R^5)$alkyl wherein $R^4$ and $R^5$ are as defined above;

X is selected from N and $CR^3$ wherein $R^3$ is selected from hydrogen, alkenyl, alkoxy, alkoxyalkoxy, alkoxyalkyl, alkyl, alkylthio, alkynyl, aryl, arylalkoxy, arylalkenyl, arylalkyl, carboxy, cyano, cycloalkyl, cycloalkylalkyl, haloalkoxy, haloalkyl, halogen, heterocycle, heterocyclealkyl, hydroxy, hydroxyalkyl, $—NR^4R^5$, and $(NR^4R^5)$alkyl wherein $R^4$ and $R^5$ are as defined above;

A and B are independently selected from hydrogen, alkenyl, alkoxy, alkoxyalkoxy, alkoxyalkyl, alkyl, alkylthio, alkynyl, aryl, arylalkoxy, arylalkenyl, arylalkyl, carboxy, cyano, cycloalkyl, cycloalkylalkyl, haloalkoxy, haloalkyl, halogen, heterocycle, heterocyclealkyl, hydroxy, hydroxyalkyl, $—NR^4R^5$, and $(NR^4R^5)$alkyl wherein $R^4$ and $R^5$ are as defined above; and D and E are independently selected from hydrogen, alkenyl, alkoxy, alkoxyalkoxy, alkoxyalkyl, alkyl, alkylthio, alkynyl, aryl, arylalkoxy, arylalkenyl, arylalkyl, carboxy, cyano, cycloalkyl, cycloalkylalkyl, haloalkoxy, haloalkyl, halogen, heterocycle, heterocyclealkyl, hydroxy, hydroxyalkyl, oxo, $—NR^4R^5$, and $(NR^4R^5)$alkyl wherein $R^4$ and $R^5$ are as defined above.

DETAILED DESCRIPTION OF THE INVENTION

All patents, patent applications, and literature references cited in the specification are herein incorporated by reference in their entirety. In the case of inconsistencies, the present disclosure, including definitions, will prevail.

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations and/or methods of use of the invention, may be made without departing from the spirit and scope thereof.

In its principle embodiment, the present invention discloses compounds of formula I:

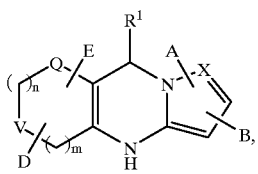

I or a pharmaceutically acceptable salt, ester, amide, or prodrug thereof wherein, n is an integer 0–1;
m is an integer 1–2;
provided that when m is 2, n is 0;
$R^1$ is selected from aryl and heterocycle;
Q is selected from C(O), S(O), and S(O)$_2$;
V is selected from C($R^6$)($R^7$), O, S, and N$R^2$, wherein $R^2$ is selected from hydrogen, alkenyl, alkoxy, alkoxyalkoxy, alkoxyalkyl, alkyl, alkynyl, aryl, arylalkoxy, arylalkenyl, arylalkyl, cyano, cycloalkyl, cycloalkylalkyl, haloalkoxy, haloalkyl, heterocycle, heterocyclealkyl, hydroxy, hydroxyalkyl, —N$R^4R^5$, and (N$R^4R^5$)alkyl wherein $R^4$ and $R^5$ are independently selected from hydrogen and lower alkyl;
$R^6$ and $R^7$ are independently selected from hydrogen, alkenyl, alkoxy, alkoxyalkoxy, alkoxyalkyl, alkyl, alkylthio, alkynyl, aryl, arylalkoxy, arylalkenyl, arylalkyl, carboxy, cyano, cycloalkyl, cycloalkylalkyl, haloalkoxy, haloalkyl, halogen, heterocycle, heterocyclealkyl, hydroxy, hydroxyalkyl, oxo, —N$R^4R^5$, and (N$R^4R^5$)alkyl wherein $R^4$ and $R^5$ are as defined above;
X is selected from N and C$R^3$ wherein $R^3$ is selected from hydrogen, alkenyl, alkoxy, alkoxyalkoxy, alkoxyalkyl, alkyl, alkylthio, alkynyl, aryl, arylalkoxy, arylalkenyl, arylalkyl, carboxy, cyano, cycloalkyl, cycloalkylalkyl, haloalkoxy, haloalkyl, halogen, heterocycle, heterocyclealkyl, hydroxy, hydroxyalkyl, —N$R^4R^5$, and (N$R^4R^5$)alkyl wherein $R^4$ and $R^5$ are as defined above;
A and B are independently selected from hydrogen, alkenyl, alkoxy, alkoxyalkoxy, alkoxyalkyl, alkyl, alkylthio, alkynyl, aryl, arylalkoxy, arylalkenyl, arylalkyl, carboxy, cyano, cycloalkyl, cycloalkylalkyl, haloalkoxy, haloalkyl, halogen, heterocycle, heterocyclealkyl, hydroxy, hydroxyalkyl, —N$R^4R^5$, and (N$R^4R^5$)alkyl wherein $R^4$ and $R^5$ are as defined above; and
D and E are independently selected from hydrogen, alkenyl, alkoxy, alkoxyalkoxy, alkoxyalkyl, alkyl, alkylthio, alkynyl, aryl, arylalkoxy, arylalkenyl, arylalkyl, carboxy, cyano, cycloalkyl, cycloalkylalkyl, haloalkoxy, haloalkyl, halogen, heterocycle, heterocyclealkyl, hydroxy, hydroxyalkyl, oxo, —N$R^4R^5$, and (N$R^4R^5$)alkyl wherein $R^4$ and $R^5$ are as defined above.

In another embodiment of the present invention, compounds have formula I wherein, $R^1$ is aryl; X is C$R^3$; $R^3$ is hydrogen; and A, B, D, E, Q, V, m, and n are as defined in formula I.

In another embodiment of the present invention, compounds have formula I wherein, $R^1$ is heterocycle; X is C$R^3$; $R^3$ is hydrogen; and A, B, D, E, Q, V, m, and n are as defined in formula I.

In a preferred embodiment, compounds of the present invention have formula II:

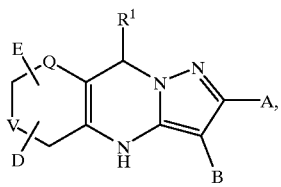

II or a pharmaceutically acceptable salt, ester, amide, or prodrug thereof wherein, $R^1$ is selected from aryl and heterocycle;
Q is selected from C(O), S(O), and S(O)$_2$;
V is selected from C($R^6$)($R^7$), O, S, and N$R^2$, wherein $R^2$ is selected from hydrogen, alkenyl, alkoxy, alkoxyalkoxy, alkoxyalkyl, alkyl, alkynyl, aryl, arylalkoxy, arylalkenyl, arylalkyl, cyano, cycloalkyl, cycloalkylalkyl, haloalkoxy, haloalkyl, heterocycle, heterocyclealkyl, hydroxy, hydroxyalkyl, —N$R^4R^5$, and (N$R^4R^5$)alkyl wherein $R^4$ and $R^5$ are independently selected from hydrogen and lower alkyl;
$R^6$ and $R^7$ are independently selected from hydrogen, alkenyl, alkoxy, alkoxyalkoxy, alkoxyalkyl, alkyl, alkylthio, alkynyl, aryl, arylalkoxy, arylalkenyl, arylalkyl, carboxy, cyano, cycloalkyl, cycloalkylalkyl, haloalkoxy, haloalkyl, halogen, heterocycle, heterocyclealkyl, hydroxy, hydroxyalkyl, oxo, —N$R^4R^5$, and (N$R^4R^5$)alkyl wherein $R^4$ and $R^5$ are as defined above;
A and B are independently selected from hydrogen, alkenyl, alkoxy, alkoxyalkoxy, alkoxyalkyl, alkyl, alkylthio, alkynyl, aryl, arylalkoxy, arylalkenyl, arylalkyl, carboxy, cyano, cycloalkyl, cycloalkylalkyl, haloalkoxy, haloalkyl, halogen, heterocycle, heterocyclealkyl, hydroxy, hydroxyalkyl, —N$R^4R^5$, and (N$R^4R^5$)alkyl wherein $R^4$ and $R^5$ are as defined above; and
D and E are independently selected from hydrogen, alkenyl, alkoxy, alkoxyalkoxy, alkoxyalkyl, alkyl, alkylthio, alkynyl, aryl, arylalkoxy, arylalkenyl, arylalkyl, carboxy, cyano, cycloalkyl, cycloalkylalkyl, haloalkoxy, haloalkyl, halogen, heterocycle, heterocyclealkyl, hydroxy, hydroxyalkyl, oxo, —N$R^4R^5$, and (N$R^4R^5$)alkyl wherein $R^4$ and $R^5$ are as defined above.

In another preferred embodiment of the present invention, compounds have formula II wherein, $R^1$ is heterocycle; Q is C(O); and A, B, D, E, and V are as defined in formula I.

In another preferred embodiment of the present invention, compounds have formula II wherein, $R^1$ is heterocycle; Q is S(O); and A, B, D, E, and V are as defined in formula I.

In another preferred embodiment of the present invention, compounds have formula II wherein, $R^1$ is heterocycle; Q is S(O)$_2$; and A, B, D, E, and V are as defined in formula I.

In another preferred embodiment of the present invention, compounds have formula II wherein, $R^1$ is heterocycle; Q is C(O); V is S; and A, B, D, and E are as defined in formula I.

In another preferred embodiment of the present invention, compounds have formula II wherein, $R^1$ is heterocycle; Q is C(O); V is S; and A, B, D, and E are hydrogen.

In another preferred embodiment of the present invention, compounds have formula II wherein, $R^1$ is heterocycle; Q is C(O); V is CH$_2$; and A, B, D, and E are as defined in formula I.

In another preferred embodiment of the present invention, compounds have formula II wherein, $R^1$ is heterocycle; Q is C(O); V is $CH_2$; B is alkyl; D is alkyl; and A and B are as defined in formula I.

In another preferred embodiment of the present invention, compounds have formula II wherein, $R^1$ is heterocycle; Q is C(O); V is $CH_2$; B is alkyl; D is alkyl; and A and B are hydrogen.

In another preferred embodiment of the present invention, compounds have formula II wherein, $R^1$ is heterocycle; Q is C(O); V is $CH_2$; and A, B, D, and E are hydrogen.

In another preferred embodiment of the present invention, compounds have formula II wherein, $R^1$ is heterocycle; Q is $S((O)_2$; V is $CH_2$; and A, B, D, and E are as defined in formula I.

In another preferred embodiment of the present invention, compounds have formula II wherein, $R^1$ is heterocycle; Q is $S((O)_2$; V is $CH_2$; and A, B, D, and E are hydrogen.

In another preferred embodiment of the present invention, compounds have formula II wherein, $R^1$ is aryl; Q is C(O); and A, B, D, E, and V are as defined in formula I.

In another preferred embodiment of the present invention, compounds have formula II wherein, $R^1$ is aryl; Q is C(O); V is S; and A, B, D, and E are as defined in formula I.

In another preferred embodiment of the present invention, compounds have formula II wherein, $R^1$ is aryl; Q is C(O); V is S; and A, B, D, and E are hydrogen.

In another preferred embodiment of the present invention, compounds have formula II wherein, $R^1$ is aryl; Q is C(O); V is $CH_2$; and A, B, D, and E are as defined in formula I.

In another preferred embodiment of the present invention, compounds have formula II wherein, $R^1$ is aryl; Q is C(O); V is $CH_2$; D is alkyl; E is alkyl; and A and B are as defined in formula I.

In another preferred embodiment of the present invention, compounds have formula II wherein, $R^1$ is aryl; Q is C(O); V is $CH_2$; D is alkyl; E is alkyl; and A and B are hydrogen.

In another preferred embodiment of the present invention, compounds have formula II wherein, $R^1$ is aryl; Q is C(O); V is $CH_2$; B is aryl; and A, D, and E are as defined in formula I.

In another preferred embodiment of the present invention, compounds have formula II wherein, $R^1$ is aryl; Q is C(O); V is $CH_2$; B is aryl; and A, D, and E are hydogen.

In another preferred embodiment of the present invention, compounds have formula II wherein, $R^1$ is aryl; Q is C(O); V is $CH_2$; B is heterocycle; and A, D, and E are as defined in formula I.

In another preferred embodiment of the present invention, compounds have formula II wherein, $R^1$ is aryl; Q is C(O); V is $CH_2$; B is heterocycle; and A, D, and E are hydogen.

In another preferred embodiment of the present invention, compounds have formula II wherein, $R^1$ is aryl; Q is C(O); V is $CH_2$; B is halogen; and A, D, and E are as defined in formula I.

In another preferred embodiment of the present invention, compounds have formula II wherein, $R^1$ is aryl; Q is C(O); V is $CH_2$; B is halogen; and A, D, and E are hydogen.

In another preferred embodiment of the present invention, compounds have formula II wherein, $R^1$ is aryl; Q is C(O); V is $CH_2$; and A, B, D, and E are hydrogen.

In another preferred embodiment of the present invention, compounds have formula II wherein, $R^1$ is aryl; Q is S(O); and A, B, D, E, and V are as defined in formula I.

In another preferred embodiment of the present invention, compounds have formula II wherein, $R^1$ is aryl; Q is $S(O)_2$; and A, B, D, E, and V are as defined in formula I.

In another preferred embodiment of the present invention, compounds have formula II wherein, $R^1$ is aryl; Q is $S(O)_2$,; V is $CH_2$; and A, B, D, and E are as defined in formula I.

In another preferred embodiment of the present invention, compounds have formula II wherein, $R^1$ is aryl; Q is $S(O)_2$; V is $CH_2$; and A, B, D, and E are hydrogen.

In another preferred embodiment, compounds of the present invention have formula III:

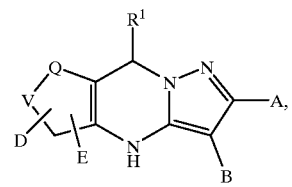

III or a pharmaceutically acceptable salt, ester, amide, or prodrug thereof wherein, $R^1$ is selected from aryl and heterocycle;

Q is selected from C(O), S(O), and $S((O)_2$;

V is selected from $C(R^6)(R^7)$, O, S, and $NR^2$, wherein $R^2$ is selected from hydrogen, alkenyl, alkoxy, alkoxyalkoxy, alkoxyalkyl, alkyl, alkynyl, aryl, arylalkoxy, arylalkenyl, arylalkyl, cyano, cycloalkyl, cycloalkylalkyl, haloalkoxy, haloalkyl, heterocycle, heterocyclealkyl, hydroxy, hydroxyalkyl, $-NR^4R^5$, and $(NR^4R^5)$alkyl wherein $R^4$ and $R^5$ are independently selected from hydrogen and lower alkyl;

$R^6$ and $R^7$ are independently selected from hydrogen, alkenyl, alkoxy, alkoxyalkoxy, alkoxyalkyl, alkyl, alkylthio, alkynyl, aryl, arylalkoxy, arylalkenyl, arylalkyl, carboxy, cyano, cycloalkyl, cycloalkylalkyl, haloalkoxy, haloalkyl, halogen, heterocycle, heterocyclealkyl, hydroxy, hydroxyalkyl, oxo, $-NR^4R^5$, and $(NR^4R^5)$alkyl wherein $R^4$ and $R^5$ are as defined above;

A and B are independently selected from hydrogen, alkenyl, alkoxy, alkoxyalkoxy, alkoxyalkyl, alkyl, alkylthio, alkynyl, aryl, arylalkoxy, arylalkenyl, arylalkyl, carboxy, cyano, cycloalkyl, cycloalkylalkyl, haloalkoxy, haloalkyl, halogen, heterocycle, heterocyclealkyl, hydroxy, hydroxyalkyl, $-NR^4R^5$, and $(NR^4R^5)$alkyl wherein $R^4$ and $R^5$ are as defined above; and D and E are independently selected from hydrogen, alkenyl, alkoxy, alkoxyalkoxy, alkoxyalkyl, alkyl, alkylthio, alkynyl, aryl, arylalkoxy, arylalkenyl, arylalkyl, carboxy, cyano, cycloalkyl, cycloalkylalkyl, haloalkoxy, haloalkyl, halogen, heterocycle, heterocyclealkyl, hydroxy, hydroxyalkyl, oxo, $-NR^4R^5$, and $(NR^4R^5)$alkyl wherein $R^4$ and $R^5$ are as defined above.

In another preferred embodiment of the present invention, compounds have formula III wherein, $R^1$ is heterocycle; Q is C(O); and A, B, D, E, and V are as defined in formula I.

In another preferred embodiment of the present invention, compounds have formula III wherein, $R^1$ is heterocycle; Q is S(O); and A, B, D, E, and V are as defined in formula I.

In another preferred embodiment of the present invention, compounds have formula III wherein, $R^1$ is heterocycle; Q is $S(O)_2$; and A, B, D, E, and V are as defined in formula I.

In another preferred embodiment of the present invention, compounds have formula III wherein, $R^1$ is aryl; Q is C(O); and A, B, D, E, and V are as defined in formula I.

In another preferred embodiment of the present invention, compounds have formula III wherein, $R^1$ is aryl; Q is C(O); V is O; and A, B, D, and E are as defined in formula I.

In another preferred embodiment of the present invention, compounds have formula III wherein, $R^1$ is aryl; Q is C(O); V is O; and A, B, D, and E are hydrogen.

In another preferred embodiment of the present invention, compounds have formula III wherein, $R^1$ is aryl; Q is S(O); and A, B, D, E, and V are as defined in formula I.

In another preferred embodiment of the present invention, compounds have formula III wherein, $R^1$ is aryl; Q is $S((O)_2)$; and A, B, D, E, and V are as defined in formula I.

In another preferred embodiment, compounds of the present invention have formula IV:

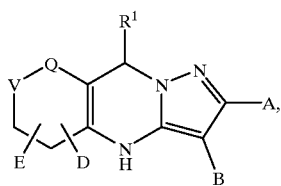

IV or a pharmaceutically acceptable salt, ester, amide, or prodrug thereof wherein, $R^1$ is selected from aryl and heterocycle;

Q is selected from C(O), S(O), and $S(O)_2$;

V is selected from $C(R^6)(R^7)$, O, S, and $NR^2$, wherein $R^2$ is selected from hydrogen, alkenyl, alkoxy, alkoxyalkoxy, alkoxyalkyl, alkyl, alkynyl, aryl, arylalkoxy, arylalkenyl, arylalkyl, cyano, cycloalkyl, cycloalkylalkyl, haloalkoxy, haloalkyl, heterocycle, heterocyclealkyl, hydroxy, hydroxyalkyl, $-NR^4R^5$, and $(NR^4R^5)$alkyl wherein $R^4$ and $R^5$ are independently selected from hydrogen and lower alkyl;

$R^6$ and $R^7$ are independently selected from hydrogen, alkenyl, alkoxy, alkoxyalkoxy, alkoxyalkyl, alkyl, alkylthio, alkynyl, aryl, arylalkoxy, arylalkenyl, arylalkyl, carboxy, cyano, cycloalkyl, cycloalkylalkyl, haloalkoxy, haloalkyl, halogen, heterocycle, heterocyclealkyl, hydroxy, hydroxyalkyl, oxo, $-NR^4R^5$, and $(NR^4R^5)$alkyl wherein $R^4$ and $R^5$ are as defined above;

A and B are independently selected from hydrogen, alkenyl, alkoxy, alkoxyalkoxy, alkoxyalkyl, alkyl, alkylthio, alkynyl, aryl, arylalkoxy, arylalkenyl, arylalkyl, carboxy, cyano, cycloalkyl, cycloalkylalkyl, haloalkoxy, haloalkyl, halogen, heterocycle, heterocyclealkyl, hydroxy, hydroxyalkyl, $-NR^4R^5$, and $(NR^4R^5)$alkyl wherein $R^4$ and $R^5$ are as defined above; and D and E are independently selected from hydrogen, alkenyl, alkoxy, alkoxyalkoxy, alkoxyalkyl, alkyl, alkylthio, alkynyl, aryl, arylalkoxy, arylalkenyl, arylalkyl, carboxy, cyano, cycloalkyl, cycloalkylalkyl, haloalkoxy, haloalkyl, halogen, heterocycle, heterocyclealkyl, hydroxy, hydroxyalkyl, oxo, $-NR^4R^5$, and $(NR^4R^5)$alkyl wherein $R^4$ and $R^5$ are as defined above.

In another preferred embodiment of the present invention, compounds have formula IV wherein, $R^1$ is heterocycle; Q is C(O); A, B, D, and E are as defined in formula I; and V is as defined in formula IV.

In another preferred embodiment of the present invention, compounds have formula IV wherein, $R^1$ is heterocycle; Q is S(O); A, B, D, and E are as defined in formula I; and V is as defined in formula IV.

In another preferred embodiment of the present invention, compounds have formula IV wherein, $R^1$ is heterocycle; Q is $S(O)_2$; A, B, D, and E are as defined in formula I; and V is as defined in formula IV.

In another preferred embodiment of the present invention, compounds have formula IV wherein, $R^1$ is aryl; Q is C(O); A, B, D, and E are as defined in formula I; and V is as defined in formula IV.

In another preferred embodiment of the present invention, compounds have formula IV wherein, $R^1$ is aryl; Q is S(O); A, B, D, and E are as defined in formula I; and V is as defined in formula IV.

In another preferred embodiment of the present invention, compounds have formula IV wherein, $R^1$ is aryl; Q is $S(O)_2$; A, B, D, and E are as defined in formula I; and V is as defined in formula IV.

Another embodiment of the present invention relates to pharmaceutical compositions comprising a therapeutically effective amount of a compound of formula I–IV or a pharmaceutically acceptable salt, ester, amide, or prodrug thereof in combination with a pharmaceutically acceptable carrier.

Another embodiment of the invention relates to a method of treating male sexual dysfunction including, but not limited to, male erectile dysfunction and premature ejaculation comprising administering a therapeutically effective amount of a compound of formula I–IV or a pharmaceutically acceptable salt, ester, amide, or prodrug thereof.

Another embodiment of the invention relates to a method of treating female sexual dysfunction including, but not limited to, female anorgasmia, clitoral erectile insufficiency, vaginal engorgement, dyspareunia, and vaginismus comprising administering a therapeutically effective amount of a compound of formula I–IV or a pharmaceutically acceptable salt, ester, amide, or prodrug thereof.

Yet another embodiment of the invention relates to a method of treating asthma, epilepsy, hypertension, Raynaud's syndrome, migraine, pain, eating disorders, urinary incontinence, finctional bowel disorders, neurodegeneration and stroke comprising administering a therapeutically effective amount of a compound of formula I–IV or a pharmaceutically acceptable salt, ester, amide, or prodrug thereof.

Definition of Terms

As used throughout this specification and the appended claims, the following terms have the following meanings.

The term "alkenyl," as used herein, refers to a straight or branched chain hydrocarbon containing from 2 to 10 carbons and containing at least one carbon—carbon double bond formed by the removal of two hydrogens. Representative examples of "alkenyl" include, but are not limited to, ethenyl, 2-propenyl, 2-methyl-2-propenyl, 3-butenyl, 4-pentenyl, 5-hexenyl, 2-heptenyl, 2-methyl-1-heptenyl, 3-decenyl and the like.

The term "alkenyloxy," as used herein, refers to an alkenyl group, as defined herein, appended to the parent molecular moiety through an oxy group, as defined herein. Representative examples of alkenyloxy include, but are not limited to, propen-3-yloxy (allyloxy), buten-4-yloxy, and the like.

The term "alkoxy," as used herein, refers to an alkyl group, as defined herein, appended to the parent molecular moiety through an oxy group, as defined herein. Representative examples of alkoxy include, but are not limited to, methoxy, ethoxy, propoxy, 2-propoxy, butoxy, tert-butoxy, pentyloxy, hexyloxy and the like.

The term "alkoxyalkoxy," as used herein, refers to an alkoxy group, as defined herein, appended to the parent molecular moiety through another alkoxy group, as defined herein. Representative examples of alkoxyalkoxy include, but are not limited to, tert-butoxymethoxy, 2-ethoxyethoxy, 2-methoxyethoxy, methoxymethoxy, and the like.

The term "alkoxyalkyl," as used herein, refers to an alkoxy group, as defined herein, appended to the parent molecular moiety through an alkyl group, as defined herein. Representative examples of alkoxyalkyl include, but are not limited to, tert-butoxymethyl, 2-ethoxyethyl, 2-methoxyethyl, methoxymethyl, and the like.

The term "alkoxycarbonyl," as used herein, refers to an alkoxy group, as defined herein, appended to the parent molecular moiety through a carbonyl group, as defined herein. Representative examples of alkoxycarbonyl include, but are not limited to, methoxycarbonyl, ethoxycarbonyl, tert-butoxycarbonyl, and the like.

The term "alkyl," as used herein, refers to a straight or branched chain hydrocarbon containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl, and the like.

The term "alkylcarbonyl," as used herein, refers to an alkyl group, as defined herein, appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl, 1-oxopentyl, and the like.

The term "alkylcarbonyloxy," as used herein, refers to an alkylcarbonyl group, as defined herein, appended to the parent molecular moiety through an oxy group, as defined herein. Representative examples of alkylcarbonyloxy include, but are not limited to, acetyloxy, ethylcarbonyloxy, tert-butylcarbonyloxy, and the like.

The term "alkylsulfinyl," as used herein, refers to an alkyl group, as defined herein, appended to the parent molecular moiety through a sulfinyl group, as defined herein. Representative examples of alkylsulfinyl include, but are not limited, methylsulfinyl, ethylsulfinyl, and the like.

The term "alkylsulfonyl," as used herein, refers to an alkyl group, as defined herein, appended to the parent molecular moiety through a sulfonyl group, as defined herein. Representative examples of alkylsulfonyl include, but are not limited to, methylsulfonyl, ethylsulfonyl, and the like.

The term "alkylthio," as used herein, refers to an alkyl group, as defined herein, appended to the parent molecular moiety through a thio moiety, as defined herein. Representative examples of alkylthio include, but are not limited, methylthio, ethylthio, tert-butylthio, hexylthio, and the like.

The term "alkynyl," as used herein, refers to a straight or branched chain hydrocarbon group containing from 2 to 10 carbon atoms and containing at least one carbon—carbon triple bond. Representative examples of alkynyl include, but are not limited, to acetylenyl, 1-propynyl, 2-propynyl, 3-butynyl, 2-pentynyl, 1-butynyl and the like.

The term "aryl," as used herein, refers to a monocyclic carbocyclic ring system or a bicyclic carbocyclic fused ring system having one or more aromatic rings. Representative examples of aryl include, azulenyl, indanyl, indenyl, naphthyl, phenyl, tetrahydronaphthyl, and the like.

The aryl groups of this invention can be substituted with 1, 2, 3, 4, or 5 substituents independently selected from alkenyl, alkenyloxy, alkoxy, alkoxyalkoxy, alkoxycarbonyl, alkyl, alkylcarbonyl, alkylcarbonyloxy, alkylsulfinyl, alkylsulfonyl, alkylthio, alkynyl, aryl, aryloxy, azido, arylalkoxy, arylalkyl, aryloxy, carboxy, cyano, formyl, halogen, haloalkyl, haloalkoxy, hydroxy, hydroxyalkyl, mercapto, nitro, sulfamyl, sulfo, sulfonate, —NR$^{80}$R$^{81}$ (wherein, R$^{80}$ and R$^{81}$ are independently selected from hydrogen, alkyl, alkylcarbonyl, aryl, arylalkyl and formyl), and —C(O)NR$^{82}$R$^{83}$ (wherein, R$^{82}$ and R$^{83}$ are independently selected from hydrogen, alkyl, alkylcarbonyl, aryl, arylalkyl, and formyl).

The term "arylalkenyl," as used herein, refers to an aryl group, as defined herein, appended to the parent molecular moiety through an alkenyl group, as defined herein. Representative examples of arylalkenyl include, but are not limited to, 2-phenylethenyl, 3-phenylpropen-2-yl, 2-naphth-2-ylethenyl, and the like.

The term "arylalkoxy," as used herein, refers to an aryl group, as defined herein, appended to the parent molecular moiety through an alkoxy group, as defined herein. Representative examples of arylalkoxy include, but are not limited to, 2-phenylethoxy, 3- naphth-2-ylpropoxy, 5-phenylpentyloxy, and the like.

The term "arylalkoxycarbonyl," as used herein, refers to an arylalkoxy group, as defined herein, appended to the parent molecular moiety through a carbonyl group, as defined herein. Representative examples of arylalkoxy include, but are not limited to, benzyloxycarbonyl, naphth-2-ylmethoxycarbonyl, and the like.

The term "arylalkyl," as used herein, refers to an aryl group, as defined herein, appended to the parent molecular moiety through an alkyl group, as defined herein. Representative examples of arylalkyl include, but are not limited to, benzyl, 2-phenylethyl, 3-phenylpropyl, 2-naphth-2-ylethyl, and the like.

The term "aryloxy," as used herein, refers to an aryl group, as defined herein, appended to the parent molecular moiety through an oxy group, as defined herein. Representative examples of aryloxy include, but are not limited to, phenoxy, naphthyloxy, and the like.

The term "azido," as used herein, refers to an —N$_3$ group.

The term "carbonyl," as used herein, refers to a —C(O)— group.

The term "carboxy," as used herein, refers to a —CO$_2$H group.

The term "carboxy protecting group," as used herein, refers to a carboxylic acid protecting ester group employed to block or protect the carboxylic acid functionality while the reactions involving other finctional sites of the compound are carried out. Carboxy-protecting groups are disclosed in T. H. Greene and P. G. M. Wuts, Protective Groups in Organic Synthesis, 2nd edition, John Wiley & Sons, New York (1991), which is hereby incorporated herein by reference. In addition, a carboxy-protecting group can be used as a prodrug whereby the carboxy-protecting group can be readily cleaved in vivo, for example by enzymatic hydrolysis, to release the biologically active parent. T. Higuchi and V. Stella provide a thorough discussion of the prodrug concept in "Pro-drugs as Novel Delivery Systems", Vol 14 of the A.C.S. Symposium Series, American Chemical Society (1975), which is hereby incorporated herein by reference. Such carboxy-protecting groups are well known to those skilled in the art, having been extensively used in the protection of carboxyl groups in the penicillin and cephalosporin fields, as described in U.S. Pat. Nos. 3,840,556 and 3,719,667, the disclosures of which are hereby incorporated herein by reference. Examples of esters useful as prodrugs for compounds containing carboxyl groups can be found on pages 14–21 of "Bioreversible Carriers in Drug Design: Theory and Application", edited by E. B. Roche, Pergamon Press, New York (1987), which is hereby incorporated herein by reference. Representative carboxy-protecting groups are loweralkyl (e.g., methyl, ethyl or tertiary butyl and the like); benzyl (phenylmethyl) and substituted benzyl derivatives thereof such substituents are selected from alkoxy, alkyl, halogen, and nitro groups and the like.

The term "cyano," as used herein, refers to a —CN group.

The term "cycloalkyl," as used herein, refers to a saturated cyclic hydrocarbon group containing from 3 to 8 carbons. Representative examples of cycloalkyl include, cyclopropyl, cyclobutyl, cyclopentyl, cyclohexyl, cycloheptyl, and cyclooctyl.

The term "cycloalkylalkyl," as used herein, refers to cycloalkyl group, as defined herein, appended to the parent molecular moiety through an alkyl group, as defined herein. Representative examples of cycloalkylalkyl include, but are not limited to, cyclopropylmethyl, 2-cyclobutylethyl, cyclopentylmethyl, cyclohexylmethyl and 4-cycloheptylbutyl, and the like.

The term "formyl," as used herein, refers to a —C(O)H group.

The term "halo" or "halogen," as used herein, refers to —Cl, —Br, —I or —F.

The term "haloalkyl," as used herein, refers to at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, 2-chloro-3-fluoropentyl, and the like.

The term "haloalkoxy," as used herein, refers to at least one halogen, as defined herein, appended to the parent molecular moiety through an alkoxy group, as defined herein. Representative examples of haloalkoxy include, but are not limited to, 2-chloroethoxy, difluoromethoxy, 1,2-difluoroethoxy, 2,2,2-trifluoroethoxy, trifluoromethoxy, and the like.

The term "heterocycle," as used herein, refers to a monocyclic- or a bicyclic-ring system. Monocyclic ring systems are exemplified by any 5 or 6 membered ring containing 1, 2, 3, or 4 heteroatoms independently selected from oxygen, nitrogen and sulfur. The 5 membered ring has from 0–2 double bonds and the 6 membered ring has from 0–3 double bonds. Representative examples of monocyclic ring systems include, but are not limited to, azetidine, azepine, aziridine, diazepine, 1,3-dioxolane, dioxane, dithiane, furan, imidazole, imidazoline, imidazolidine, isothiazole, isothiazoline, isothiazolidine, isoxazole, isoxazoline, isoxazolidine, morpholine, oxadiazole, oxadiazoline, oxadiazolidine, oxazole, oxazoline, oxazolidine, piperazine, piperidine, pyran, pyrazine, pyrazole, pyrazoline, pyrazolidine, pyridine, pyrimidine, pyridazine, pyrrole, pyrroline, pyrrolidine, tetrahydrofuran, tetrahydrothiophene, tetrazine, tetrazole, thiadiazole, thiadiazoline, thiadiazolidine, thiazole, thiazoline, thiazolidine, thiophene, thiomorpholine, thiomorpholine sulfone, thiopyran, triazine, triazole, trithiane, and the like. Bicyclic ring systems are exemplified by any of the above monocyclic ring systems fused to an aryl group as defined herein, a cycloalkyl group as defined herein, or another monocyclic ring system as defined herein. Representative examples of bicyclic ring systems include but are not limited to, for example, benzimidazole, benzothiazole, benzothiadiazole, benzothiophene, benzoxadiazole, benzoxazole, benzofuran, benzopyran, benzothiopyran, benzodioxine, 1,3-benzodioxole, cinnoline, indazole, indole, indoline, indolizine, naphthyridine, isobenzofuran, isobenzothiophene, isoindole, isoindoline, isoquinoline, phthalazine, pyranopyridine, quinoline, quinolizine, quinoxaline, quinazoline, tetrahydroisoquinoline, tetrahydroquinoline, thiopyranopyridine, and the like.

The heterocycle groups of this invention can be substituted with 1, 2, or 3 substituents independently selected from alkenyl, alkenyloxy, alkoxy, alkoxyalkoxy, alkoxycarbonyl, alkyl, alkylcarbonyl, alkylcarbonyloxy, alkylsulfinyl, alkylsulfonyl, alkylthio, alkynyl, aryl, azido, arylalkoxy, arylalkoxycarbonyl, arylalkyl, aryloxy, carboxy, cyano, formyl, halogen, haloalkyl, haloalkoxy, hydroxy, hydroxyalkyl, mercapto, nitro, sulfamyl, sulfo, sulfonate, —NR$^{80}$R$^{81}$ (wherein, R$^{80}$ and R$^{81}$ are independently selected from hydrogen, alkyl, alkylcarbonyl, aryl, arylalkyl and formyl), and —C(O)NR$^{82}$R$^{83}$ (wherein, R$^{82}$ and R$^{83}$ are independently selected from hydrogen, alkyl, aryl, and arylalkyl).

The term "heterocyclealkyl," as used herein, refers to a heterocycle, as defined herein, appended to the parent molecular moiety through an alkyl group, as defined herein. Representative examples of heterocyclealkyl include, but are not limited to, pyrid-3-ylmethyl, 2-pyrimidin-2-ylpropyl, and the like.

The term "hydroxy," as used herein, refers to an —OH group.

The term "hydroxyalkyl," as used herein, refers to a hydroxy group, as defined herein, appended to the parent molecular moiety through an alkyl group, as defined herein. Representative examples of hydroxyalkyl include, but are not limited to, hydroxymethyl, 2-hydroxyethyl, 3-hydroxypropyl, and the like.

The term "lower alkyl," as used herein, is a subset of alkyl as defined herein and refers to a straight or branched chain hydrocarbon group containing from 1 to 4 carbon atoms. Representative examples of lower alkyl include, but are not limited to, methyl, ethyl, n-propyl, iso-propyl, n-butyl, iso-butyl, tert-butyl, and the like.

The term "mercapto," as used herein, refers to a —SH group.

The term "(NR$^4$R$^5$)alkyl," as used herein, refers to a —NR$^4$R$^5$ group, as defined herein, appended to the parent molecular moiety through an alkyl group, as defined herein. Representative examples of (NR$^4$R$^5$)alkyl include, but are not limited to, aminomethyl, dimethylaminomethyl, 2-(amino)ethyl, 2-(dimethylamino)ethyl, and the like.

The term "nitro," as used herein, refers to a —NO$_2$ group.

The term "oxo," as used herein, refers to a =O moiety.

The term "oxy," as used herein, refers to a —O— moiety.

The term "sulfamyl," as used herein, refers to a —SO$_2$NR$^{94}$R$^{95}$ group, wherein, R$^{94}$ and R$^{95}$ are independently selected from hydrogen, alkyl, aryl, and arylalkyl, as defined herein.

The term "sulfinyl," as used herein, refers to a —S(O)— group.

The term "sulfo," as used herein, refers to a —SO₃H group.

The term "sulfonate," as used herein, refers to a —S((O)₂OR⁹⁶ group, wherein, R⁹⁶ is selected from alkyl, aryl, and arylalkyl, as defined herein.

The term "sulfonyl," as used herein, refers to a —SO₂— group.

The term "thio," as used herein, refers to a —S— moiety.

Preferred compounds of formula I include, but are not limited to:

9-(3-bromo-4-fluorophenyl)-5,6,7,9-tetrahydropyrazolo[5,1-b]quinazolin-8(4H)-one,
9-(3-bromo-4-fluorophenyl)-5,9-dihydro-4H-pyrazolo[1,5-a]thiopyrano[3,4-d]pyrimidin-8(7H)-one,
9-(1-naphthyl)-5,6,7,9-tetrahydropyrazolo[5,1-b]quinazolin-8(4H)-one,
9-(2-naphthyl)-5,6,7,9-tetrahydropyrazolo[5,1-b]quinazolin-8(4H)-one,
9-(3,4-dibromophenyl)-5,6,7,9-tetrahydropyrazolo[5,1-b]quinazolin-8(4H)-one,
9-(3,4-dichlorophenyl)-5,6,7,9-tetrahydropyrazolo[5,1-b]quinazolin-8(4H)-one,
9-(3-bromophenyl)-5,6,7,9-tetrahydropyrazolo[5,1-b]quinazolin-8(4H)-one,
9-(3-chlorophenyl)-5,6,7,9-tetrahydropyrazolo[5,1-b]quinazolin-8(4H)-one,
9-[4-chloro-3-(trifluoromethyl)phenyl]-5,6,7,9-tetrahydropyrazolo[5,1-b]quinazolin-8(4H)-one,
9-[4-fluoro-3-(trifluoromethyl)phenyl]-5,6,7,9-tetrahydropyrazolo[5,1-b]quinazolin-8(4H)-one,
9-[³-(trifluoromethoxy)phenyl]-5,6,7,9-tetrahydropyrazolo[5,1-b]quinazolin-8(4H)-one,
9-(3-cyanophenyl)-5,6,7,9-tetrahydropyrazolo[5,1-b]quinazolin-8(4H)-one,
9-(3-methylphenyl)-5,6,7,9-tetrahydropyrazolo[5,1-b]quinazolin-8(4H)-one,
8-(3-bromo-4-fluorophenyl)-5,8-dihydro-4H,7H-furo[3,4-d]pyrazolo[1,5-a]pyrimidin-7-one,
(−) 9-(3-bromo-4-fluorophenyl)-5,6,7,9-tetrahydropyrazolo[5,1-b]quinazolin-8(4H)-one,
(+) 9-(3-bromo-4-fluorophenyl)-5,6,7,9-tetrahydropyrazolo[5,1-b]quinazolin-8(4H)-one,
9-(3-bromo-4-fluorophenyl)-5,6,7,9-tetrahydro-4H-pyrazolo[1,5-a]thiopyrano[3,2-d]pyrimidine 8,8-dioxide,
3-bromo-9-(3-bromo-4-fluorophenyl)-5,6,7,9-tetrahydropyrazolo[5,1-b]quinazolin-8(4H)- one,
9-(3-chloro-4-fluorophenyl)-5,6,7,9-tetrahydropyrazolo[5,1-b]quinazolin-8(4H)-one,
9-(3,4-difluorophenyl)-5,6,7,9-tetrahydropyrazolo[5,1-b]quinazolin-8(4H)-one,
9-(4-fluorophenyl)-5,6,7,9-tetrahydropyrazolo[5,1-b]quinazolin-8(4H)-one,
9-(4-chloro-3-nitrophenyl)-5,6,7,9-tetrahydropyrazolo[5,1-b]quinazolin-8(4H)-one,
9-(⁴-chloro-3-fluorophenyl)-7,7-dimethyl-5,6,7,9-tetrahydropyrazolo[5,1-b]quinazolin-8(4H)-one,
9-(3-bromo-4-fluorophenyl)-7,7-dimethyl-5,6,7,9-tetrahydropyrazolo[5,1-b]quinazolin-8(4H)-one,
9-[4-fluoro-3-(trifluoromethyl)phenyl]-7,7-dimethyl-5,6,7,9-tetrahydropyrazolo[5,1-b]quinazolin-8(4H)-one,
9-(3,4-dichlorophenyl)-7,7-dimethyl-5,6,7,9-tetrahydropyrazolo[5,1-b]quinazolin-8(4H)-one,
9-(4-chloro-3-nitrophenyl)-7,7-dimethyl-5,6,7,9-tetrahydropyrazolo[5,1-b]quinazolin-8(4H)-one,
9-(3,4-dibromophenyl)-7,7-dimethyl-5,6,7,9-tetrahydropyrazolo[5,1-b]quinazolin-8(4H)-one,
9-[3-fluoro-4-(trifluoromethyl)phenyl]-7,7-dimethyl-5,6,7,9-tetrahydropyrazolo[5,1-b]quinazolin-8(4H)-one,
9-(3-nitrophenyl)-7,7-dimethyl-5,6,7,9-tetrahydropyrazolo[5,1-b]quinazolin-8(4H)-one,
9-(3-cyanophenyl)-7,7-dimethyl-5,6,7,9-tetrahydropyrazolo[5,1-b]quinazolin-8(4H)-one,
7,7-dimethyl-9-(5-nitro-3-thienyl)-5,6,7,9-tetrahydropyrazolo[5,1-b]quinazolin-8(4H)-one,
9-(5-bromo-2-hydroxyphenyl)-7,7-dimethyl-5,6,7,9-tetrahydropyrazolo[5,1-b]quinazolin-8(4H)-one,
9-(5-chloro-2-hydroxyphenyl)-7,7-dimethyl-5,6,7,9-tetrahydropyrazolo[5,1-b]quinazolin-8(4H)-one,
9-(2-hydroxy-5-nitrophenyl)-7,7-dimethyl-5,6,7,9-tetrahydropyrazolo[5,1-b]quinazolin-8(4H)-one,
9-(3,5-dibromo-2-hydroxyphenyl)-7,7-dimethyl-5,6,7,9-tetrahydropyrazolo[5,1-b]quinazolin-8(4H)-one,
9-(3-bromo-5-chloro-2-hydroxyphenyl)-7,7-dimethyl-5,6,7,9-tetrahydropyrazolo [5,1-b]quinazolin-8(4H)-one,
9-(3,5-dichloro-2-hydroxyphenyl)-7,7-dimethyl-5,6,7,9-tetrahydropyrazolo [5,1-b]quinazolin-8(4H)-one,
9-(3,4,5-trifluorophenyl)-7,7-dimethyl-5,6,7,9-tetrahydropyrazolo[5,1-b]quinazolin-8(4H)-one,
9-(3,4-dichlorophenyl)-3-(3-fluorophenyl)-5,6,7,9-tetrahydropyrazolo[5,1-b]quinazolin-8(4H)-one,
9-(3,4-dichlorophenyl)-3-(3-chlorophenyl)-5,6,7,9-tetrahydropyrazolo[5,1-b]quinazolin-8(4H)-one,
9-(3,4-dichlorophenyl)-3-(4-carboxyphenyl)-5,6,7,9-tetrahydropyrazolo [5,1-b]quinazolin-8(4H)-one,
9-(3,4-dichlorophenyl)-3-(2-thienyl)-5,6,7,9-tetrahydropyrazolo[5,1-b]quinazolin-8(4H)-one,
3-bromo-9-(3,4-dichlorophenyl)-5,6,7,9-tetrahydropyrazolo[5,1-b]quinazolin-8(4H)-one and pharmaceutically acceptable salts, esters, amides, or prodrugs thereof.

Preparation of Compounds of the Invention

The compounds and processes of the present invention will be better understood in connection with the following synthetic schemes and methods which illustrate a means by which the compounds of the invention can be prepared.

The compounds of this invention can be prepared by a variety of synthetic routes. Representative procedures are shown in Schemes 1–20.

Scheme 1

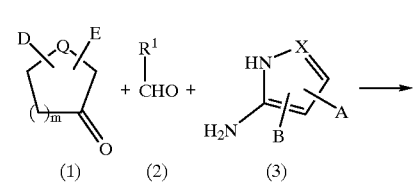

-continued

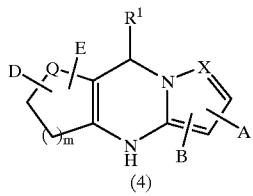
(4)

Fused pyrimidines of general formula (4), wherein $R^1$, X, Q, A, B, D and E are as defined in formula I and m is an integer 1–2, can be prepared according to the method of Scheme 1. A carbonyl component of general formula (1) can be treated with an aldehyde of general formula (2) and an amino heterocycle of general formula (3) in a solvent such as ethanol, acetonitrile or dimethylformamide with heating to provide fused pyrimidines of general formula (4).

Scheme 2

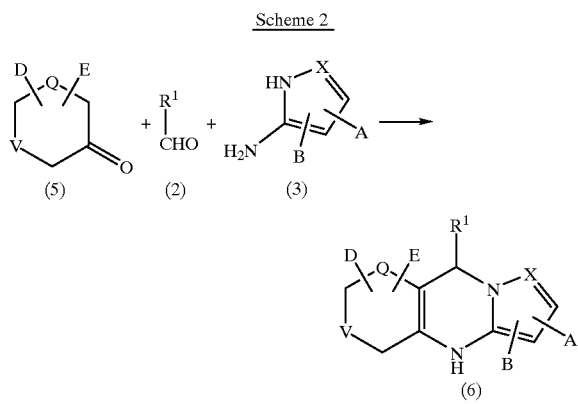

Fused pyrimidines of general formula (6), wherein $R^1$, X, Q, V, A, B, D, and E are as defined in formula I, can be prepared according to the method of Scheme 2. A carbonyl component of general formula (5) can be treated with an aldehyde of general formula (2) and an amino heterocycle of general formula (3) in a solvent such as ethanol, acetonitrile or dimethylformamide with heating to provide fused pyrimidines of general formula (6). Carbonyl components of general formula (5) may be prepared using the procedures described in (Dodd, J. H., Journal of Heterocyclic Chemistry 27 (1990) 1453; Terasawa, T., Journal of Organic Chemistry 42 (1977) 1163).

Scheme 3

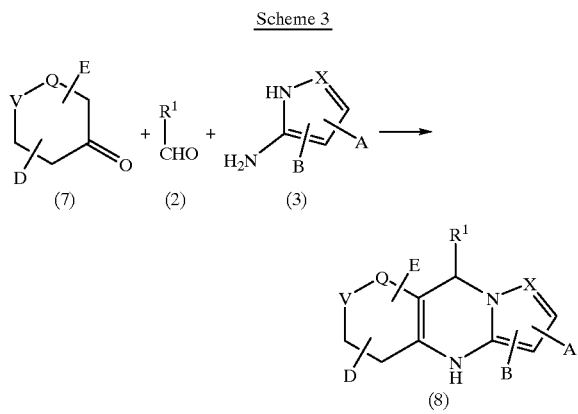

Fused pyrimidines of general formula (8), wherein $R^1$, X, Q, V, A, B, D, and E are as defined in formula I, can be prepared according to the method of Scheme 3. A carbonyl component of general formula (7) can be treated with an aldehyde of general formula (2) and an amino heterocycle of general formula (3) in a solvent such as ethanol, acetonitrile or dimethylformamide with heating to provide fused pyrimidines of general formula (8). Carbonyl components of general formula (7) may be prepared as described in (Nakagawa, S., Heterocycles 13 (1979) 477; D'Angelo, J., Tetrahedron Letters 32 (1991) 3063).

Scheme 4

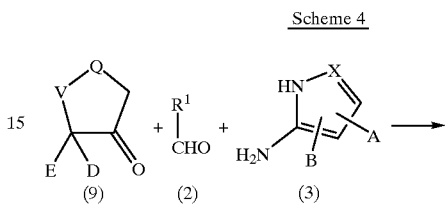

Fused pyrimidines of general formula (10), wherein $R^1$, X, Q, V, A, B, D, and E are as defined in formula I, can be prepared according to the method of Scheme 4. A carbonyl component of general formula (9) can be treated with an aldehyde of general formula (2) and an amino heterocycle of general formula (3) in a solvent such as ethanol, acetonitrile or dimethylformamide with heating to provide fused pyrimidines of general formula (10).

Scheme 5

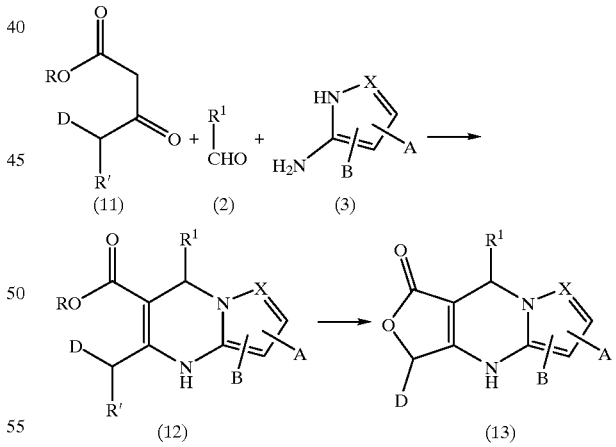

Fused pyrimidines of general formula (13), wherein $R^1$, X, A, B, and D are as defined in formula I, can be prepared according to the method of Scheme 5. A dicarbonyl component of general formula (11), wherein $R^1$ is selected from Cl and OAc and R is selected from lower alkyl, cyanoalkyl, and carboxy protecting group, can be treated with an aldehyde of general formula (2) and an amino heterocycle of general formula (3) in a solvent such as ethanol, acetonitrile or dimethylformamide with heating to provide fused pyrimidines of general formula (12). In the case where $R^1$ is OAc, cleavage of the acetyl group may be required to induce cyclization to provide fused pyrimidines of general formula (13). In the case where $R^1$ is Cl, cyclization can proceed directly without the isolation of (12) to provide fused pyrimidines of general formula (13).

Many of the starting aryl and heteroaryl aldehydes necessary to carry out the methods described in the preceeding and following Schemes may be purchased from commercial sources or may be synthesized by known procedures found in the chemical literature. Appropriate literature references for the preparation of aryl and heteroaryl aldehydes may be found in the following section or in the Examples. For starting materials not previously described in the literature the following Schemes are intended to illustrate their preparation through a general method.

The preparation of aldehydes used to synthesize many preferred compounds of the invention may be found in the following literature references: Pearson, Org. Synth. Coll. Vol V (1 973), 117; Nwaukwa, Tetrahedron Lett. (1 982), 23, 313 1; Badder, J. Indian Chem. Soc. (1976), 53,1053; Khanna, J. Med. Chem. (1997), 40,1634; Rinkes, Recl. Trav. Chim. Pays-Bas (1945), 64, 205; van der Lee, Recl. Trav. Chim. Pays-Bas (1926), 45, 687; Widman, Chem. Ber. (1882), 15,167; Hodgson, J. Chem. Soc. (1927), 2425; Clark, J. Fluorine Chem. (1990), 50, 411; Hodgson, J. Chem. Soc. (1929), 1635; Duff, J. Chem. Soc. (1951), 1512; Crawford, J. Chem. Soc. (1956), 2155; Tanouchi, J. Med. Chem.(1981),24,1149; Bergmann,J.Am.Chem.Soc.(1959), 81,5641; Other: Eistert, Chem. Ber. (1964), 97,1470; Sekikawa, Bull. Chem. Soc. Jpn. (1959), 32, 551.

Scheme 6

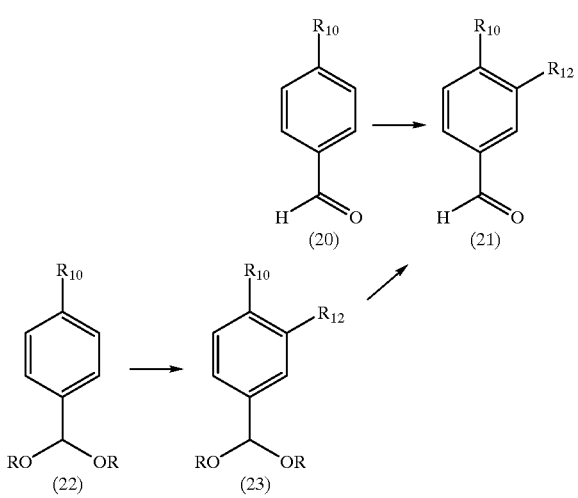

Meta, para-disubstituted aldehydes of general formula (21), wherein $R_{10}$ is selected from alkyl, haloalkyl, halo, haloalkoxy, alkoxy, alkylthio, —$NR_{82}R_{83}$, and —$C(O)NR_{82}R_{83}$ wherein $R_{82}$ and $R_{83}$ are independently selected from hydrogen, alkyl, alkylcarbonyl, aryl, arylalkyl, and formyl and $R_{12}$ is selected from nitro, halo, and alkylcarbonyl, can be prepared according to the method described in Scheme 6. A para substituted aldehyde of general formula (20) or the corresponding acetal protected aldehyde of general formula (22), wherein R is selected from alkyl or together with the oxygen atoms to which they are attached form a 5 or 6 membered ring wherein 1,3-dioxolanes are preferred, may by subjected to conditions of an electrophilic aromatic substitution reaction to provide aldehydes of general formula (21) or protected aldehydes of general formula (23). Preferred protecting groups for compounds of general formula (22) and (23) include dimethyl or diethyl acetals or the 1,3-dioxolanes. These protecting groups can be introduced at the beginning and removed at the end to provide substituted aldehydes of general formula (21) using methods well known to those skilled in the art of organic chemistry.

Scheme 7

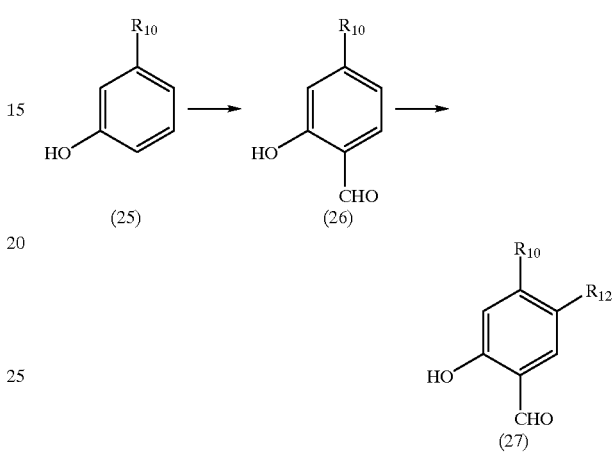

Aldehydes of general formula (27), wherein $R_{10}$ is selected from alkyl, haloalkyl, halo, haloalkoxy, alkoxy, alkylthio, —$NR_{82}R_{83}$, and —$C(O)NR_{82}R_{83}$ wherein $R_{82}$ and $R_{83}$ are independently selected from hydrogen, alkyl, alkylcarbonyl, aryl, arylalkyl, and formyl and $R_{12}$ is selected from nitro, halo, and alkylcarbonyl, can be prepared by the method described in Scheme 7. A meta substituted phenol (25) is converted to the para substituted salicylaldehyde (26) by reaction with a base such as sodium hydroxide and a reagent such as trichloromethane or tribromomethane, known as the Reimer-Tiemann reaction. An alternate set of reaction conditions involves reaction with magnesium methoxide and paraformaldehyde (Aldred, J. Chem. Soc. Perkin Trans. 1 (1994), 1823). The aldehyde (26) may be subjected to conditions of an electrophilic aromatic substitution reaction to provide meta, para disubstituted salicylaldehydes of general formula (27).

Scheme 8

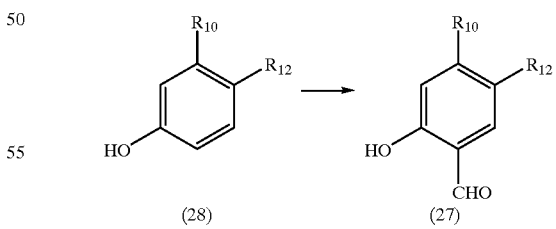

An alternative method of preparing meta, para disubstituted salicylaldehydes of general formula (27), wherein $R_{10}$ is selected from alkyl, haloalkyl, halo, haloalkoxy, alkoxy, alkylthio, —$NR_{82}R_{83}$, and —$C(O)NR_{82}R_{83}$, wherein $R_{82}$ and $R_{83}$ are independently selected from hydrogen, alkyl, alkylcarbonyl, aryl, arylalkyl, and formyl and $R_{12}$ is selected from nitro, halo, and alkylcarbonyl, can be used as described in Scheme 8. A meta, para disubstituted phenol of general formula (28) can be reacted with a base such as sodium hydroxide and a reagent such as trichloromethane or tribromomethane, known as the Reimer-Tiemann reaction, to provide disubstituted salicylaldehydes of general formula (27). An alternate set of reaction conditions involves reaction with magnesium methoxide and paraformaldehyde (Aldred, J. Chem. Soc. Perkin Trans. 1 (1994), 1823).

Scheme 9

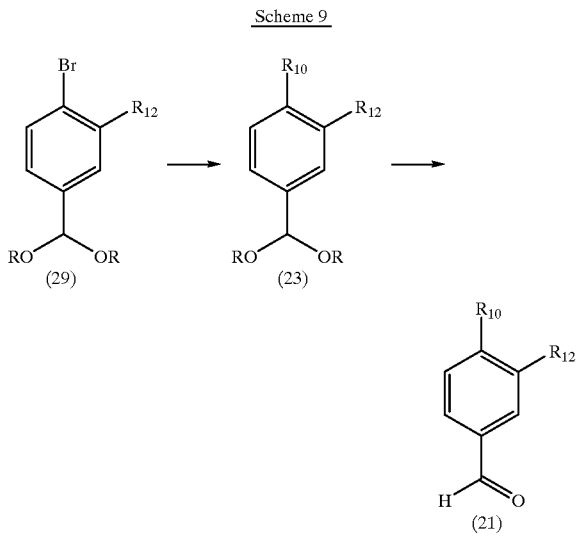

An alternative method of preparing benzaldehydes of general formula (21), wherein $R_{12}$ is selected from alkyl, haloalkyl, chlorine, fluorine, haloalkoxy, alkoxy, alkylthio, nitro, alkylcarbonyl, arylcarbonyl, —$NR_{82}R_{83}$, and —$C(O)NR_{82}R_{83}$ wherein $R_{82}$ and $R_{83}$ are independently selected from hydrogen, alkyl, alkylcarbonyl, aryl, arylalkyl, and formyl, and $R_{10}$ is selected from alkyl, hydroxyalkyl, alkylthio, alkylcarbonyl, and formyl, is described in Scheme 9. Protected benzaldehydes of general formula (29), wherein R is selected from alkyl or together with the oxygen atoms to which they are attached form a 5 or 6 membered ring wherein 1,3-dioxolanes are preferred, can be converted to the 3,4-disubstituted benzaldehyde of general formula (23) via conversion of the bromide to an intermediate lithio or magnesio derivative, followed by reaction with an appropriate electrophile such as an aldehyde, dialkyldisulfide, a Weinreb amide, dimethylformamide, an alkyl halide or other electrophile followed by deprotection of the acetal to provide benzaldehydes of general formula (21).

Scheme 10

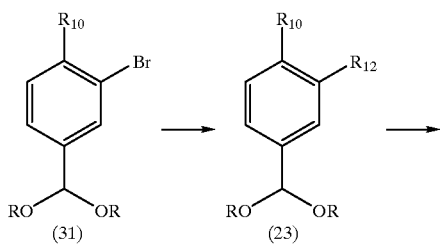

-continued

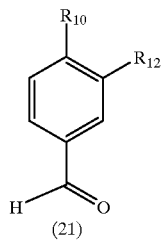

An alternative method of preparing benzaldehydes of general formula (21), wherein $R_{10}$ is selected from alkyl, haloalkyl, chlorine, fluorine, haloalkoxy, alkoxy, alkylthio, —$NR_{82}R_{83}$, and —$C(O)NR_{82}R_{83}$ wherein $R_{82}$ and $R_{83}$ are independently selected from hydrogen, alkyl, alkylcarbonyl, aryl, arylalkyl, and formyl, $R_{12}$ is selected from alkyl, hydroxyalkyl, alkylthio, alkylcarbonyl, arylcarbonyl, and formyl, can be used as described in Scheme 10. Protected benzaldehydes of general formula (31), wherein R is selected from alkyl or together with the oxygen atoms to which they are attached form a 5 or 6 membered ring wherein 1,3-dioxolanes are preferred can be processed as described in Scheme 9 to provide benzaldehydes of general formula (21).

Scheme 11

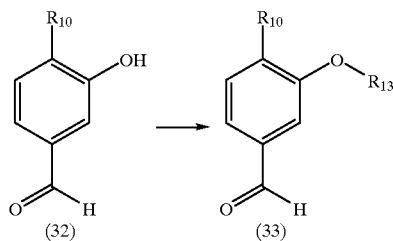

Benzaldehydes of general formula (33), wherein $R_{10}$ is selected from hydrogen, alkyl, alkylsulfonyl, aryl, heteroaryl, cyano, haloalkyl, halo, haloalkoxy, nitro, alkoxy, alkylthio, —$NR_{82}R_{83}$, and —$C(O)NR_{82}R_{83}$ wherein $R_{82}$ and $R_{83}$ are independently selected from hydrogen, alkyl, alkylcarbonyl, aryl, arylalkyl, and formyl, and $R_{13}$ is selected from hydrogen, alkyl, arylalkyl, and haloalkyl wherein preferred haloalkyl groups are selected from difluoromethyl, 2,2,2-trifluoroethyl and bromodifluoromethyl, can be prepared as described in Scheme 11. 3-Hydroxybenzaldehyde of general formula (32) can be treated with suitable alkylating reagents such as benzylbromide, iodomethane, 2-iodo- 1,1,1-trifluoroethane, chlorodifluoromethane, or dibromodifluoromethane in the presence of base such as potassium carbonate, potassium tert-butoxide or sodium tert-butoxide, to provide benzaldehydes of general formula (33). The synthesis of useful 3-hydroxybenzaldehydes of general formula (32) may be found in the following literature references: J. Chem. Soc. (1923), 2820; J. Med Chem. (1986), 29,1982; Monatsh. Chem. (1963), 94,1262; Justus Liebigs Ann. Chem. (1897), 294, 381; J. Chem. Soc. Perkin Trans. 1 (1990), 315; Tetrahedron Lett. (1990), 5495; J. Chem. Soc. Perkin Trans. 1 (1981), 2677.

Scheme 12

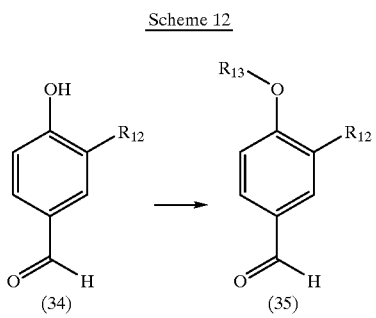

Benzaldehydes of general formula (35), wherein $R_{12}$ is selected from hydrogen, alkyl, alkylsulfonyl, aryl, heteroaryl, cyano, haloalkyl, halo, haloalkoxy, nitro, alkoxy, alkylthio, —$NR_{82}R_{83}$, and —$C(O)NR_{82}R_{83}$ wherein $R_{82}$ and $R_{83}$ are independently selected from hydrogen, alkyl, alkylcarbonyl, aryl, arylalkyl, and formyl, and $R_{13}$ is selected from hydrogen, alkyl, arylalkyl, and haloalkyl wherein preferred haloalkyl groups are selected from difluoromethyl, 2,2,2-trifluoroethyl, and bromodifluoromethyl, can be prepared as described in Scheme 12. 4-Hydroxybenzaldehydes of general formula (34) can be treated with suitable alkylating reagents such as benzylbromide, iodomethane, 2-iodo-1,1,1-trifluoroethane, chlorodifluoromethane, or dibromodifluoromethane, in the presence of base such as potassium carbonate, potassium tert-butoxide or sodium tert-butoxide to provide benzaldehydes of general formula (35). The synthesis of useful 4-hydroxybenzaldehydes of general formula (34) may be found in the following literature references: Angyal, J. Chem. Soc. (1950), 2141; Ginsburg, J. Am. Chem. Soc. (1951), 73, 702; Claisen, Justus Liebigs Ann. Chem. (1913), 401,107; Nagao, Tetrahedron Lett. (1980), 21, 4931; Ferguson, J. Am. Chem. Soc. (1950), 72, 4324; Barnes, J. Chem. Soc. (1950), 2824; Villagomez-Ibarra, Tetrahedron (1995), 51, 9285; Komiyama, J. Am. Chem. Soc. (1983), 105, 2018; DE 87255; Hodgson, J. Chem. Soc. (1929), 469; Hodgson, J. Chem. Soc. (1929), 1641.

Scheme 13

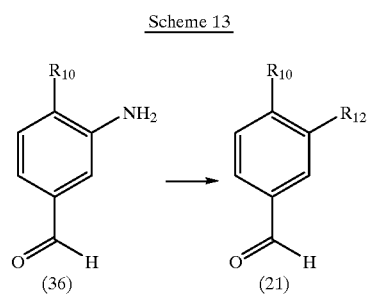

An alternate method for introduction of substituents at the 3-position of benzaldehydes of general formula (21), wherein $R_{10}$ is selected from hydrogen, alkyl, alkylsulfonyl, aryl, heteroaryl, cyano, haloalkyl, halo, haloalkoxy, nitro, alkoxy, alkylthio, and —$C(O)NR_{82}R_{83}$, wherein $R_{82}$ and $R_{83}$ are independently selected from hydrogen, alkyl, alkylcarbonyl, aryl, arylalkyl, and formyl can be used as described in Scheme 13. This method, also known as the Sandmeyer reaction, involves converting 3-amino benzaldehydes of general formula (36) to an intermediate diazonium salt with sodium nitrite. The diazonium salts can be treated with a bromine or iodine source to provide the bromide or iodide. The Sandmeyer reaction and conditions for effecting the transformation are well known to those skilled in the art of organic chemistry. The types of $R_{12}$ substituents that may be introduced in this fashion include cyano, hydroxy, or halo. In order to successfully carry out this transformation it may in certain circumstances be advantageous to perform the Sandmeyer reaction on a protected aldehyde. The resulting iodide or bromide can be treated with unsaturated halides, boronic acids or tin reagents in the presence of a palladium catalyst such as tetrakis(triphenylphosphine)palladium ((O) to provide benzaldehydes of general formula (21). The diazonium salts may also be treated directly with unsaturated halides, boronic acids or tin reagents in the presence of a palladium catalyst such as tetrakis(triphenylphosphine)palladium ((O) to provide benzaldehydes of general formula (21).

Scheme 14

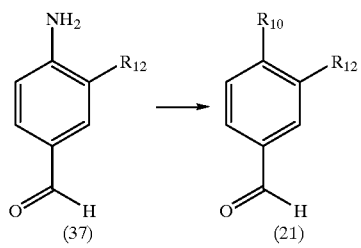

An alternate method for introduction of substituents at the 4-position of benzaldehydes of general formula (21), wherein $R_{12}$ is selected from hydrogen, alkyl, alkylsulfonyl, aryl, heteroaryl, cyano, haloalkyl, halo, haloalkoxy, nitro, alkoxy, alkylthio, and —$C(O)NR_{82}R_{83}$, wherein $R_{82}$ and $R_{83}$ are independently selected from hydrogen, alkyl, alkylcarbonyl, aryl, arylalkyl, and formyl, can be used as described in Scheme 14. This method, also known as the Sandmeyer reaction, involves converting 4-amino benzaldehydes of general formula (37) to an intermediate diazonium salt with sodium nitrite and then treating the diazonium salts in a similar manner as that described in Scheme 13. The types of $R_{10}$ substituents that may be introduced in this fashion include cyano, hydroxy, or halo. The Sandmeyer reaction and conditions for effecting the transformation are well known to those skilled in the art of organic chemistry. In order to successfully carry out this transformation it may in certain circumstances be advantageous to perform the Sandmeyer reaction on a protected aldehyde.

Scheme 15

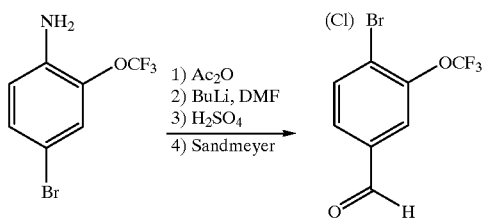

4-Bromo-3-(trifluoromethoxy)benzaldehyde or 4-chloro-3-(trifluoromethoxy)benzaldehyde can be prepared as described in Scheme 15. The commercially available 4-bromo-2-(trifluoromethoxy)aniline can be protected on the amino group with a suitable N-protecting group well known to those skilled in the art of organic chemistry such as acetyl or tert-butoxycarbonyl. The bromine can then be converted to the lithio or magnesio derivative and reacted directly with dimethylformamide to provide the 4-aminoprotected-3-(trifluoromethoxy)benzaldehyde derivative. Removal of the N-protecting group followed by conversion of the amine to a bromide or chloride via the Sandmeyer method of Scheme 14 provides 4-bromo-3-(trifluoromethoxy)benzaldehyde or 4-chloro-3-(trifluoromethoxy)benzaldehyde.

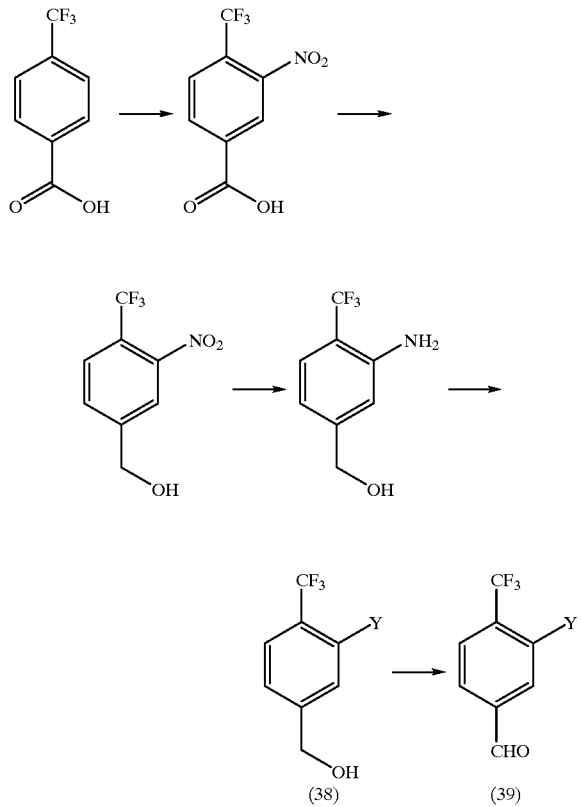

Scheme 16

4-Trifluoromethylbenzaldehydes of general formula (39), wherein Y is selected from cyano, nitro, and halo may be prepared according to the method of Scheme 16. 4-Trifluoromethylbenzoic acid is first nitrated, using suitable conditions well known in the literature such as nitric acid with sulfuric acid, and the carboxylic acid group reduced with borane to provide 3-nitro-4-trifluoromethylbenzyl alcohol. From this benzyl alcohol may be obtained the 3-nitro-4-trifluoromethylbenzaldehyde by oxidation with typical reagents such as manganese dioxide. The nitro benzylic alcohol can be reduced to the aniline using any of a number of different conditions for effecting this transformation among which a preferred method is hydrogenation over a palladium catalyst. The aniline can be converted to either a halo or cyano substituent using the Sandmeyer reaction described in Scheme 13. Benzyl alcohols of general formula (38) can be oxidized using conditions well known to those skilled in the art such as manganese dioxide or swern conditions to provide benzaldehydes of general formula (39).

For certain aromatic ring substitutions of $R_1$ for compounds of the present invention it is preferable to effect transformations of the aromatic ring substitutions after the aldehyde has been incorporated into the core structure of the present invention. As such, compounds of the present invention may be further transformed to other distinct compounds of the present invention. These transformations involve Stille, Suzuki and Heck coupling reactions all of which are well known to those skilled in the art of organic chemistry. Shown below are some representative methods of such transformations of compounds of the present invention to other compounds of the present invention.

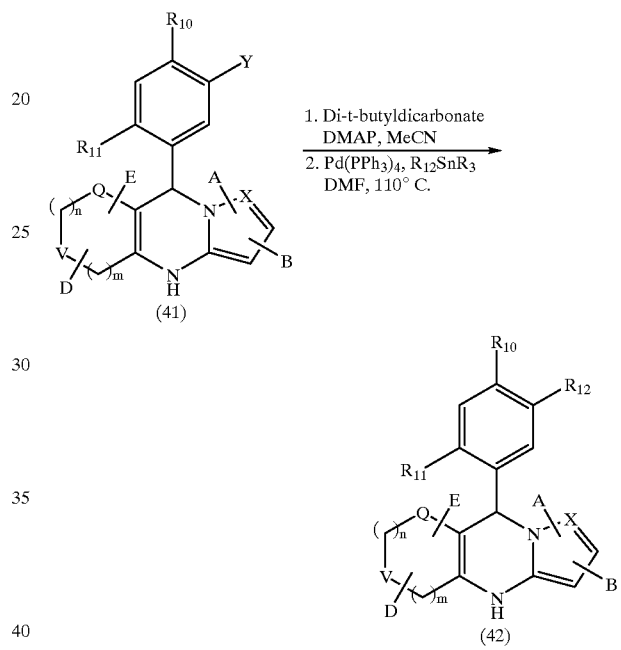

Scheme 17

Dihydropyridines of general formula (42), wherein A, B, D, E, Q, V, X, m, and n are as defined in formula I, $R_{10}$ is selected from hydrogen, alkyl, alkylcarbonyl, alkylsulfonyl, aryl, heteroaryl, cyano, haloalkyl, chlorine, fluorine, haloalkoxy, nitro, alkoxy, and alkylthio, and —C(O) $NR_{82}R_{83}$ wherein $R_{82}$ and $R_{83}$ are independently selected from hydrogen, alkyl, alkylcarbonyl, aryl, arylalkyl, and formyl, $R_{11}$ is selected from hydrogen, hydroxy, alkoxy, haloalkoxy, and arylalkoxy, $R_{12}$ is selected from alkyl, vinyl, aryl, heteroaryl, cyano and the like, can be prepared as described in Scheme 17. Compounds of general formula (41), wherein Y is selected from bromine, iodine, and triflate, are protected with a tert-butoxycarbonyl (Boc) group using standard procedures. The aromatic bromide, iodide, or triflate can be treated with a suitable tin, boronic acid, or unsaturated halide reagent in the presence of a palladium catalyst with heating in a solvent such as dimethylformamide to effect a coupling reaction that provides dihydropyridines of general formula (42). The conditions for this transformation also effect the removal of the Boc protecting group.

Scheme 18

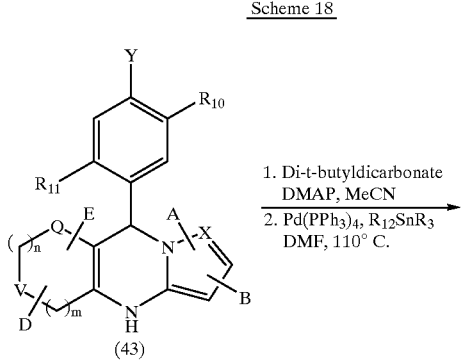

(43)

1. Di-t-butyldicarbonate DMAP, MeCN
2. Pd(PPh₃)₄, R₁₂SnR₃ DMF, 110° C.

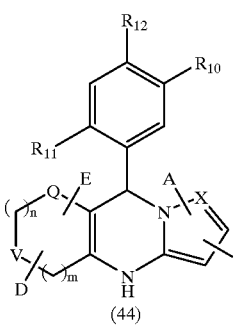

(44)

Dihydropyridines of general formula (44), wherein A, B, D, E, Q, V, X, m, and n are as defined in formula I, $R_{12}$ is selected from hydrogen, alkyl, alkylcarbonyl, alkylsulfonyl, aryl, heteroaryl, cyano, haloalkyl, chlorine, fluorine, haloalkoxy, nitro, alkoxy, alkylthio, and —C(O)NR₈₂R₈₃ wherein $R_{82}$ and $R_{83}$ are independently selected from hydrogen, alkyl, alkylcarbonyl, aryl, arylalkyl, and formyl, $R_{11}$ is selected from hydrogen, hydroxy, alkoxy, haloalkoxy, and arylalkoxy, $R_{10}$ is selected from alkyl, vinyl, aryl, heteroaryl, cyano and the like, can be prepared as described in Scheme 18. Dihydropyridines of general formula (43), wherein Y is selected from bromine, iodine, and triflate, can be protected with a tert-butoxycarbonyl (Boc) group using standard procedures. The aromatic bromide, iodide, or triflate can be reacted with a suitable tin, boronic acid, or unsaturated halide reagent in the presence of a palladium catalyst with heating in a solvent such as dimethylformanide to effect a coupling reaction that provides dihydropyridines of general formula (44). The conditions for this transformation also effect the removal of the Boc protecting group.

Scheme 19

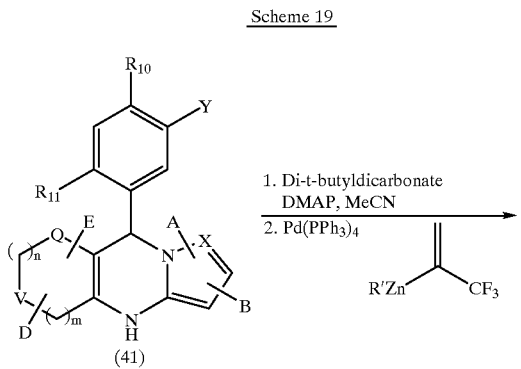

(41)

1. Di-t-butyldicarbonate DMAP, MeCN
2. Pd(PPh₃)₄

R'Zn–C(CF₃)=CH₂

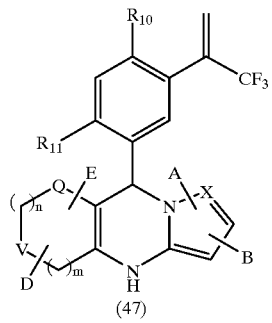

(47)

Dihydropyridines of general formula (47), wherein A, B, D, E, Q, V, X, m, and n are as defined in formula I, $R_{10}$ is selected from hydrogen, alkyl, alkylcarbonyl, alkylsulfonyl, aryl, heteroaryl, cyano, haloalkyl, chlorine, fluorine, haloalkoxy, nitro, alkoxy, alkylthio, and —C(O)NR₈₂R₈₃ wherein $R_{82}$ and $R_{83}$ are independently selected from hydrogen, alkyl, alkylcarbonyl, aryl, arylalkyl, and formyl, and $R_{11}$ is selected from hydrogen, hydroxy, alkoxy, haloalkoxy, and arylalkoxy, can be prepared as described in Scheme 19. Dihydropyridines of general formula (41), wherein Y is selected from bromine, iodine, and triflate can be protected with a tert-butoxycarbonyl (Boc) group using standard procedures. The aromatic bromide, iodide, or triflate can be treated with a suitable halozinc reagent in the presence of a palladium catalyst with heating in a solvent such as dimethylformamide to effect a coupling reaction that provides dihydropyridines of general formula (47). The conditions for this transformation also effect the removal of the Boc protecting group. The types of meta substituents that may be introduced in this fashion include trihalopropenyl and more specifically the trifluoropropenyl group.

Scheme 20

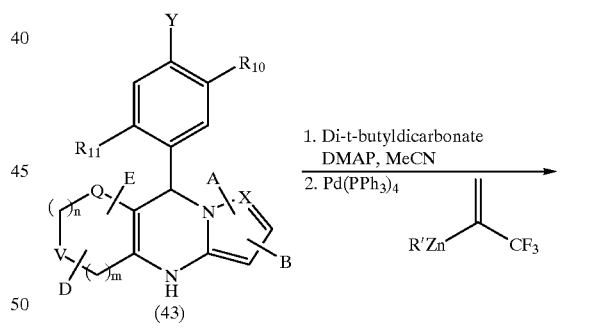

(43)

1. Di-t-butyldicarbonate DMAP, MeCN
2. Pd(PPh₃)₄

R'Zn–C(CF₃)=CH₂

(48)

Dihydropyridines of general formula (48), A, B, D, E, Q, V, X, m, and n are as defined in formula I, $R_{10}$ is selected from hydrogen, alkyl, alkylcarbonyl, alkylsulfonyl, aryl, heteroaryl, cyano, haloalkyl, chlorine, fluorine, haloalkoxy, nitro, alkoxy, alkylthio, —C(O)NR$_{12}$R$_{83}$ wherein R$_{82}$ and R$_{83}$ are independently selected from hydrogen, alkyl, alkylcarbonyl, aryl, arylalkyl, and formyl, R$_{11}$ is selected from hydrogen, hydroxy, alkoxy, haloalkoxy, and arylalkoxy, can be prepared as described in Scheme 20. Dihydropyridines of general formula (43), wherein Y is selected from bromine, iodine, and triflate can be protected with a tert-butoxycarbonyl (Boc) group using standard procedures. The aromatic bromide, iodide, or triflate can be treated with a suitable halozinc reagent in the presence of a palladium catalyst with heating in a solvent such as dimethylformamide to effect a coupling reaction that provides dihydropyridines of general formula (48). The conditions for this transformation also effect the removal of the Boc protecting group. The types of para substituents that may be introduced in this fashion include trihalopropenyl and more specifically the trifluoropropenyl group.

The compounds and processes of the present invention will be better understood by reference to the following examples, which are intended as an illustration of and not a limitation upon the scope of the invention. Further, all citations herein are incorporated by reference.

EXAMPLE 1

9-(4-bromo-3-fluorophenyl)-5,6,7,9-tetrahydropyrazolo[5,1-b]quinazolin-8(4H)-one A solution of 1,3-cyclohexanedione(0.56 g, 5 mmol), 3-bromo-4-fluorobenzaldehyde(1.01 g, 5 mmol), and 3-aminopyrazole (0.41 g, 5 mmol) in ethanol (5 mL) was heated at reflux for 24 hours. After the reaction mixture was allowed to cool to ambient temperature, the volatiles were evaporated at reduced pressure and the resulting residue was chromatographed on silica gel, eluting with 5% ethanol/methylene chloride to provide 0.9 g (49 %) of the title compound.

$^1$H NMR (DMSO-d$_6$) δ 1.94 (m, 2H), 2.25 (m, 2H), 2.63 (m, 2H), 3.42 (m, 1H), 5.72 (d, 1H), 6.19 (s, 1H), 7.1 (m, 1H), 7.23 (t, 1H), 7.317.4 (dd, 1H), 10.55 (s, 1H);

MS (ESI-) m/z: 362 (M-H)$^-$;

Anal. Calcd for C$_{16}$H$_{13}$FBrN$_3$O: C, 53.06; H, 3.62; N, 11.60. Found: C, 52.92; H, 4.02; N, 11.48.

EXAMPLE 2

9-(3-bromo-4-fluorophenyl)-5,9-dihydro-4H-pyrazolo[1,5-a]thiopyrano[3,4-d]pyrimidin-8(7H)-one A solution of 3,5-thiopyrandione (0.13 g, 1 mmol), 3-bromo-4-fluorobenzaldehyde(0.203 g, 1 mmol), and 3-aminopyrazole (0.082 g, 1 mmol) in ethanol (2 mL) was heated at reflux for 24 hours. After the reaction mixture was allowed to cool to ambient temperature, the volatiles were evaporated at reduced pressure and the resulting residue was chromatographed on silica gel, eluting with 5% ethanol/methylene chloride to provide 0.045 g (12%) of the title compound.

mp 160–163° C.;

$^1$H NMR (DMSO-d$_6$) δ 3.15 (d, 1H), 3.5 (d, 1H), 3.6 (d, 1H),3.9 (d, 1H), 5.8 (d, 1H), 6.26 (s, 1H), 7.13 (m, 1H), 7.29 (t, 1H), 7.38 (d, 1H), 7.42 (dd, 1H), 10.86 (s, 1H);

MS (ESI-) m/z: 380 (M-H)$^-$;

Anal. Calcd for C$_{15}$H$_{11}$BrFN$_3$OS.0.25C$_2$H$_6$O: C, 47.52; H, 3.22; N, 10.73. Found: C, 47.57; H, 2.89; N, 10.29.

EXAMPLE 3

9-(1-naphthyl)-5,6,7,9-tetrahydropyrazolo[5,1-b]quinazolin-8(4H)-one

A solution of 1,3-cyclohexanedione(0.11 g, 1 mmol), 1-naphthaldehyde(0.16 g, 1 mmol), and 3-aminopyrazole (0.11 g, 1.27 mmol) in ethanol (10 mL) was heated at 80 ° C. in a sealed 20 mL vial for 3 days. After the reaction mixture was allowed to cool to ambient temperature, the solvent was evaporated at reduced pressure and the resulting residue was chromatographed on silica gel, eluting with 5% ethanol/methylene chloride to provide 0.14 g (44%) of the title compound.

$^1$H NMR (DMSO-d$_6$) δ 1.95 (m, 2H), 2.21 (m, 2H), 2.72 (m,2H), 5.62 (s, 1H), 7.00 (d, 1H), 7.15–7.95 (m, 7H), 8.61 (d, 1H), 10.45 (s, 1H);

MS (APCI+) m/z: 316 (M+H)$^+$;

Analysis Calculated for C$_{20}$H$_{17}$N$_3$O: C, 76.17; H, 5.43; N, 13.32. Found: C, 75.99; H, 5.48; N, 13.27.

EXAMPLE 4

9-(2-naphthyl)-5,6,7,9-tetrahydropyrazolo[5,1-b]quinazolin-8(4H)-one

2-Naphthaldehyde (0.16 g, 1 mmol) was treated according to the procedure described in Example 3 to provide 0.16 g (51%) of the title compound.

$^1$H NMR(DMSO-d$_6$) δ 1.91(m, 2H), 2.25(m, 2H), 2.68 (m,2H), 5.74(d, 1H), 6.37(s, 1H), 7.20-7.90(m, 8H), 10.50(s, 1H);

MS(APCI+) m/z: 316(M+H)$^+$;

Analysis Calculated for C$_{20}$H$_{17}$N$_3$O: C, 76.17; H, 5.43; N, 13.32. Found: C,75.97; H, 5.50; N, 13.35.

EXAMPLE 5

9-(3 4-dibromophenyl)-5,6,7,9-tetrahydropyrazolo[5,1-b]quinazolin-8(4H)-one

A solution of 1,3-cyclohexanedione(0.11 g, 1 mmol), 3,4-dibromobenzaldehyde(0.26 g, 1 mmol), and 3-aminopyrazole(0.11 g, 1.27 mmol) in ethanol (10 mL) was heated at 80 ° C. in a sealed 20 mL vial for 3 days. After the reaction mixture was allowed to cool to ambient temperature, the resulting solid was isolated by filtration and recrystallization from acetone to provide 0.23 g (56%) of the title compound.

$^1$HNMR(DMSO-d$_6$) 1.91(m, 2H), 2.25(m, 2H), 2.64(m, 2H), 5.78(d, 1H), 6.19(s, 1H), 6.95-7.65(m, 4H), 10.59(s, 1H);

MS(APCI+) m/z: 423(M+H)$^+$;

Analysis Calculated for C$_{16}$H$_{13}$Br$_2$N$_3$O: C, 45.42; H, 3.10; N, 9.93; Br, 37.77. Found: C, 45.17; H, 3.22; N, 9.88; Br, 37.59.

EXAMPLE 6

9-(3,4-dichlorophenyl)-5,6,7,9-tetrahydropyrazolo[5,1-b]quinazolin-8(4H)-one 3,4-Dichlorobenzaldehyde (0.18 g, 1 mmol) was treated according to the procedure described in Example 3 to provide 0.18 g (55%) of the title compound.

$^1$H NMR(DMSO-d$_6$) δ 1.95(m, 2H), 2.25(m, 2H), 2.64(m, 2H), 5.78(d, 1H), 6.20(s, 1H), 7.00-7.58(m, 4H), 10.50(s, 1H);

MS(APCI+) m/z: 334(M+H)$^+$;

Analysis Calculated for $C_{16}H_{13}Cl_2N_3O$: C, 57.50; H, 3.92; N, 12.57; Cl, 21.22. Found: C, 57.29; H, 4.06; N, 12.53; Cl, 21.45.

EXAMPLE 7

9-(3-bromophenyl)-5,6,7,9-tetrahydropyrazolo[5,1-b]quinazolin-8(4H)-one

3-Bromobenzaldehyde (0.19 g, 1 mmol) was treated according to the procedure described in Example 3 to provide 0.21 g (60%) of the title compound.

$^1$H NMR(DMSO-d$_6$) δ 1.93(m, 2H), 2.25(m, 2H), 2.65 (m, 2H), 5.78(d, 1H), 6.20(s, 1H), 7.05-7.40(m, 5H), 10.55 (s, 1H);

MS(APCI+) m/z: 344(M+H)$^+$;

Analysis Calculated for $C_{16}H_{14}BrN_3O$: C, 55.83; H, 4.10; N, 12.21; Br, 23.21. Found: C, 55.95; H, 4.30; N, 12.14; Br, 23.30.

EXAMPLE 8

9-(3-chlorophenyl)-5,6,7,9-tetrahydropyrazolo[5,1-b]quinazolin-8(4H)-one

3—Chlorobenzaldehyde (0.14 g, 1 mmol) was treated according to the procedure described in Example 3 to provide 0.17 g (49%) of the title compound.

$^1$H NMR(DMSO-d$_6$) δ 1.95(m, 2H), 2.25(m, 2H), 2.65(m, 2H), 5.75(d, 1H), 6.20(s, 1H), 7.02-7.38(m, 5H), 10.55(s, 1H);

MS(APCI+) m/z: 300(M+H)$^+$;

Analysis Calculated for $C_{16}H_{14}ClN_3O$: C, 64.11; H, 4.71; N, 14.02; Cl, 11.83. Found: C, 63.81; H, 4.82; N, 14.30; Cl, 11.96.

EXAMPLE 9

9-[4-chloro-3-(trifluoromethyl)phenyl]-5,6,7,9-tetrahydropyrazolo[5,1-b]quinazolin-8(4H)-one 4-Chloro-3-trifluoromethylbenzaldehyde (0.21 g, 1 mmol) was treated according to the procedure described in Example 3 to provide 0.17 g (45%) of the title compound.

$^1$H NMR(DMSO-d$_6$) δ 1.95(m, 2H), 2.25(m, 2H), 2.65(m, 2H), 5.78(d, 1H), 6.30(s, 1H), 7.30-7.61(m, 4H), 10.59(s, 1H);

MS(APCI+) m/z: 368 (M+H)$^+$;

Analysis Calculated for $C_{17}H_{13}ClF_3N_3O$: C, 55.52; H, 3.56; N, 11.43; Cl, 9.64; F, 15.50.

Found: C, 55.50; H, 3.67; N, 11.59; Cl. 9.68; F, 15.15.

EXAMPLE 10

9-[4-fluoro-3-(trifluoromethyl)phenyl]-5,6,7,9-tetrahydropyrazolo[5,1-b]quinazolin-8(4H)-one 4-Fluoro-3-trifluoromethylbenzaldehyde (0.19 g, 1 mmol) was treated according to the procedure described in Example 3 to provide 0.16 g (46%) of the title compound.

$^1$H NMR(DMSO-d$_6$) δ 1.95(m, 2H), 2.25(m, 2H), 2.65(m, 2H), 5.79(d, 1H), 6.29(s, 1H), 7.35-7.48(m, 4H), 10.60(s, 1H);

MS(APCI+) m/z: 352(M+H)$^+$;

Analysis Calculated for $C_{17}H_{13}F_4N_3O$: C, 58.12; H, 3.73; N, 11.96; F, 21.63. Found: C, 54.49; H, 3.90; N, 11.07; F, 22.79.

EXAMPLE 11

9-[3-(trifluoromethoxy)phenyl]-5,6,7,9-tetrahydropyrazolo[5,1-b]quinazolin-8(4H)-one 3-Trifluoromethoxybenzaldehyde (0.19 g, 1 mmol) was treated according to the procedure described in Example 3 to provide 0.17 g (50%) of the title compound.

$^1$H NMR(DMSO-d$_6$) δ 1.95(m, 2H), 2.25(m, 2H), 2.65(m, 2H), 5.78(d, 1H), 6.25(s, 1H), 7.05-7.40(m, 5H), 10.05(s, 1H);

MS(APCI+) m/z: 350(M+H)$^+$;

Analysis Calculated for $C_{17}H_{14}F_3N_3O_2$: C, 58.45; H, 4.04; N, 12.03; F, 16.32. Found: C, 58.43; H, 3.93; N, 11.90; F, 15.92.

EXAMPLE 12

9-(3-cyanophenyl)-5,6,7,9-tetrahydropyrazolo[5,1-b]quinazolin-8(4H)-one

3-Cyanobenzaldehyde (0.13 g, 1 mmol) was treated according to the procedure described in Example 3 to provide 0.16 g (55%) of the title compound.

$^1$H NMR(DMSO-d$_6$) δ 1.95(m, 2H), 2.25(m, 2H), 2.65(m, 2H), 5.78(d, 1H), 6.25(s, 1H), 7.30-7.66(m, 5H), 10.60(s, 1H);

MS(APCI+) m/z: 291 (M+H)$^+$;

Analysis Calculated for $C_{17}H1_4N_4O$: C, 70.33; H, 4.86; N, 19.30. Found: C, 70.31; H, 4.95; N, 19.36.

EXAMPLE 13

9-(3-methylphenyl)-5,6,7,9-tetrahydropyrazolo[5,1-b]quinazolin-8(4H)-one

3-Methylbenzaldehyde (0.12 g, 1 mmol) was treated according to the procedure described in Example 3 to provide 0.17 g (60%) of the title compound.

$^1$H NMR (DMSO-d$_6$) 1.90 (m, 2H), 2.21 (s, 3H), 2.24 (m, 2H), 2.61 (m, 2H), 5.70 (d, 1H), 6.19 (s, 1H), 6.85-7.30 (m, 5H), 10.40 (s, 1H);

MS (APCI+) m/z: 280 (M+H)$^+$;

Analysis Calculated for $C_{17}H_{17}N_3O$: C, 73.10; H, 6.13; N, 15.04. Found: C, 72.92; H, 6.17; N, 15.35.

EXAMPLE 14

8-(3-bromo-4-fluorophenyl)-5,8-dihydro-4H,7H-furo[3,4-d]pyrazolo[1,5-a]pyrimidin-7-one A solution of methyl 4-chloroacetate (0.108 g, 1 mmol), 3-bromo-4-fluorobenzaldehyde(0.203 g, 1 mmol), and 3-aminopyrazole (0.082 g, 1 mmol) in ethanol (2 mL) was heated at reflux for 24 hours. After the reaction mixture was allowed to cool to ambient temperature, the volatiles were evaporated at reduced pressure and the resulting residue was chromatographed on silica gel, eluting with 5% ethanol/methylene chloride to provide 0.045 g (12%) of the title compound.

$^1$H NMR (DMSO-d$_6$) δ 5.02 (q, 2H), 5,85 (d, 1H), 6.3 (s, 1H), 7.25 (m, 1H), 7.31 (t, 1H), 7.39 (d, 1H), 7.52 (dd, 1H), 11.08 (s, 1H);

MS (ESI+) m/z: 352 (M+H)$^+$;

Analysis Calculated for $C_{14}H_9BrFN_3O_2$: C, 48.02; H, 2.59; N, 12.00. Found: C, 48.40; H, 2.87; N, 11.65.

EXAMPLE 15

(−) 9-(3-bromo-4-fluorophenyl)-5,6,7,9-tetrahydropyrazolo[5,1-b]quinazolin-8(4H)-one The product from Example 1 (0.6 g) was chromatographed on a Chiracel OD 4.6×250 Prep Model column, eluting with 10% ethanol/hexane to provide 0.259 g of the title compound (retention time 12.0 min).

$[\alpha]^{23}_D$ −35.85° (DMSO);

$^1$H NMR (DMSO-d$_6$) δ 1.93 (m, 2H), 2.25 (m, 2H), 2.62 (m, 2H), 5.72 (d, 1H), 6.19 (s, 1H), 7.1 (m, 1H), 7.22 (t, 1H), 7.31 (d, 1H), 7.4 (dd, 1H), 10.55 (s, 1H);

MS (ESI+) m/z: 362 (M+H)$^+$;

Analysis Calculated for C$_{16}$H$_{13}$N$_3$BrFO: C, 53.06; H, 3.62; N, 11.60. Found: C, 52.83; H, 3.77; N, 11.28.

EXAMPLE 16

(+) 9-(3-bromo-4-fluorophenyl)-5,6,7,9-tetrahydropyrazolo [5,1-b]quinazolin-8(4H)-one The product from Example 1 (0.6 g) was chromatographed on a Chiracel OD 4.6×250 Prep Model column, eluting with 10% ethanol/hexane to provide 0.252 g of the title compound (retention time 14.639 min).

$[\alpha]^{23}_D$ +35.88° (DMSO);

$^1$H NMR (DMSO-d$_6$) δ 1.92 (m, 2H), 2.25 (m, 2H), 2.55 (m, 2H), 5.72 (d, 1H), 6.19 (s, 1H), 7.1 (m, 1H), 7.23 (t, 1H), 7.32 (d, 1H), 7.4 (dd, 1H), 10.55 (s, 1H);

MS (ESI+) m/z: 362 (M+H)$^+$;

Analysis Calculated for C$_{16}$H$_{13}$N$_3$BrFO: C, 53.06; H, 3.62; N, 11.60. Found: C, 52.81; H, 3.72; N, 11.54.

EXAMPLE 17

9-(3-bromo-4-fluorophenyl)-5,6,7,9-tetrahydro-4H-pyrazolo[1,5-a]thiopyrano[3,2-d]pyrimidine 8,8-dioxide A solution of tetrahydrothiopyran-3-one-1,1-dioxide (0.74 g, 5 mmol), 3-bromo-4-fluorobenzaldehyde(1.01 g, 5 mmol), and 3-aminopyrazole (0.41 g, 5 mmol) in ethanol (5 mL) was heated at reflux for 24 hours. After the reaction mixture was allowed to cool to ambient temperature, the solid that precipitated was filtered off, washed with ethanol, and dried to provide the title compound.

$^1$H NMR (DMSO-d$_6$) δ 2.23 (m, 2H), 2.63 (m, 2H), 3.26 (m, 1H), 3.42 (m, 1H), 5,63 (d, 1H), 6.32 (s, 1H), 7.22 (m, 1H), 7.3 (d, 1H), 7.31 (t, 1H), 7.48 (dd, 1H), 10.17 (s, 1H);

MS (ESI+) m/z: 400 (M+H)$^+$;

Analysis Calculated for C$_{15}$H$_{13}$N$_3$BrFO$_2$S: C, 45,11; H, 3.26; N, 10.53. Found: C, 45,13; H, 3.50; N, 10.40.

Determination of Potassium Channel Opening Activity Membrane Hyperpolarization Assays Compounds were evaluated for potassium channel opening activity using primary cultured quinea-pig urinary bladder (GPB) cells.

For the preparation of urinary bladder smooth muscle cells, urinary bladders were removed from male quinea-pigs (Hartley, Charles River, Wilmington, Mass.) weighing 300–400 g and placed in ice-cold Ca$^{2+}$-free Krebs solution (Composition, mM: KCl, 2.7; KH$_2$PO$_4$, 1.5; NaCl, 75; Na$_2$HPO$_4$, 9.6; Na$_2$HPO$_4$.7H$_2$O, 8; MgSO$_4$, 2; glucose, 5; HEPES, 10; pH 7.4). Cells were isolated by enzymatic dissociation as previously described with minor modifications in (Klockner, U. and Isenberg, G., Pflugers Arch. 1985, 405, 329–339), hereby incorporated by reference. The bladder was cut into small sections and incubated in 5 mL of the Kreb's solution containing 1 mg/mL collagenase (Sigma, St. Louis, Mo.) and 0.2 mg/mL pronase (Calbiochem, La Jolla, Calif.) with continuous stirring in a cell incubator for 30 minutes. The mixture was then centrifuged at 1300×g for 5 minutes, and the pellet resuspended in Dulbecco's PBS (GIBCO, Gaithersburg, Md.) and recentrifuged to remove residual enzyme. The cell pellet was resuspended in 5 mL growth media (composition: Dulbecco's modified Eagle's medium supplemented with 10% fetal bovine serum, 100 units/niL penicillin, 100 units/mL streptomycin and 0.25 mg/mL amphotericin B) and further dissociated by pipetting the suspension through a flame-polished Pasteur pipette and passing it through a polypropylene mesh membrane (Spectrum, Houston, Tex.). The cell density was adjusted to 100,000 cells/mL by resuspension in growth media. Cells were plated in clear-bottomed black 96-well plates (Packard) for membrane potential studies at a density of 20,000 cells/well and maintained in a cell incubator with 90% air: 10% CO$_2$ until confluent. Cells were confirmed to be of smooth muscle type by cytoskeletal staining using a monoclonal mouse anti human-α-smooth muscle actin (Biomeda, Foster City, Calif.).

Functional activity at potassium channels was measured by evaluating changes in membrane potential using the bis-oxonol dye DiBAC(4)$_3$ (Molecular Probes) in a 96-well cell-based kinetic assay system, Fluorescent Imaging Plate Reader (FLIPR) (K. S. Schroeder et al., J. Biomed. Screen., v. 1 pp. 75–81 (1996)), hereby incorporated by reference. DiBAC(4)$_3$ is an anionic potentiometric probe which partitions between cells and extracellular solution in a membrane potential-dependent manner. With increasing membrane potential (for example, K$^+$ depolarization), the probe further partitions into the cell; this is measured as an increase in fluorescence due to dye interaction with intracellular lipids and proteins. Conversely, decreasing membrane potential (hyperpolarization by potassium channel openers) evokes a decrease in fluorescence.

Confluent quinea-pig urinary bladder cells cultured in black clear-bottomed 96-well plates were rinsed twice with 200 mL assay buffer (composition, mM: HEPES, 20; NaCl, 120; KCl, 2; CaCl$_2$, 2; MgCl$_2$, 1; glucose, 5; pH 7.4 at 25 °C.) containing 5 μM DiBAC(4)$_3$ and incubated with 180 mL of the buffer in a cell incubator for 30 minutes at 37 ° C. to ensure dye distribution across the membrane. After recording the baseline fluorescence for 5 minutes, the reference or test compounds, prepared at 10 times the concentration in the assay buffer, were added directly to the wells. Changes in fluorescence were monitored for an additional 25 minutes. Hyperpolarization responses were corrected for any background noise and were normalized to the response observed with 10 μM of the reference compound P1075, N"-cyano-N-(tert-pentyl)-N'-(3-pyridinyl)quanidine, which was assigned as 100%. P1075 is a potent opener of smooth muscle K$_{ATP}$ channels (Quast et al., Mol. Pharmacol., v. 43 pp. 474–481 (1993)) and was prepared using the procedures described in (Manley, J. Med. Chem. (1992) 35, 2327–2340), hereby incorporated by reference.

Routinely, five concentrations of P1075 or test compounds (log or half-log dilutions) were evaluated and the maximal steady-state hyperpolarization values (expressed as % relative to P1075) plotted as a function of concentration. The EC$_{50}$ (concentration that elicites 50% of the maximal response for the test sample) values were calculated by non-linear regression analysis using a four parameter sigmoidal equation. The maximal response of each compound (expressed as % relative to P1075) is reported. Stock solutions of compounds were prepared in 100% DMSO and further dilutions were carried out in the assay buffer and added to a 96-well plate. The maximal steady-state hyperpolarization values (expressed as % relative to P1075) and the $EC_{50}$ values for representative compounds of the present invention are shown in Table 1.

TABLE 1

Membrane Hyperpolarization (MHP) in Guinea-Pig Bladder (GPB) Cells

| Example # | Maximal Response (% P1075) | $EC_{50}(\mu M)$ |
|---|---|---|
| 1 | 87 | 0.031 |
| 2 | 100 | 0.040 |
| 3 | 34 | 24 |
| 4 | 96 | 0.429 |
| 5 | 98 | 0.122 |
| 6 | 95 | 0.130 |
| 7 | 98 | 0.550 |
| 8 | 92 | 1.12 |
| 9 | 94 | 0.187 |
| 10 | 100 | 0.290 |
| 11 | 90 | 1.71 |
| 12 | 85 | 2.86 |
| 13 | 50 | 10 |
| 14 | 89 | 0.258 |
| 15 | 103 | 0.051 |
| 16 | 105 | 0.020 |
| 17 | 89 | 0.910 |

In vitro Functional models

Compounds of the present invention were evaluated for functional potassium channel opening activity using tissue strips obtained from Landrace pig bladders.

Landrace pig bladders were obtained from female Landrace pigs of 9–30 kg. Landrace pigs wer eutanized with an intraperitoneal injection of pentobarbital solution, Somlethal®, J. A. Webster Inc., Sterling Mass. The entire bladder was removed and immediately placed into Krebs Ringer bicarbonate solution (composition, mM: NaCl, 120; $NaHCO_3$, 20; dextrose, 11; KCl, 4.7; $CaCl_2$, 2.5; $MgSO_4$, 1.5; $KH_2PO_4$, 1.2; $K_2EDTA$, 0.01, equilibrated with 5% $CO_2/95\%$ $O_2$ pH 7.4 at 37 ° C.). Propranolol (0.004 mM) was included in all of the assays to block β-adrenoceptors. The trigonal and dome portions were discarded. Strips 3–5 mm wide and 20 mm long were prepared from the remaining tissue cut in a circular fashion. The mucosal layer was removed. One end was fixed to a stationary glass rod and the other to a Grass FT03 transducer at a basal preload of 1.0 gram. Two parallel platinum electrodes were included in the stationary glass rod to provide field stimulation of 0.05 Hz, 0.5 milli-seconds at 20 volts. This low frequency stimulation produced a stable twitch response of 100–500 centigrams. Tissues were allowed to equilibrate for at least 60 minutes and primed with 80 mM KCl. A control concentration response curve (cumulative) was generated for each tissue using the potassium channel opener P1075 as the control agonist. P1075 completely eliminated the stimulated twitch in a dose dependent fashion over a concentration range of $10^{-9}$ to $10^{-5}$M dissolved in DMSO using ½ log increments. After a 60 minute rinsing period, a concentration response curve (cumulative) was generated for the test agonist in the same fashion as that used for the control agonist P1075. The maximal efficacy of each compounds (expressed as % relative to P1075) is reported. The amount of agent necessary to cause 50% of the agent's maximal response ($ED_{50}$) was calculated using "ALLFIT" (DeLean et al., Am. J. Physiol., 235, E97 (1980)), hereby incorporated by reference, and agonist potencies were expressed as $pD_2$ (the negative logarithm). Agonist potencies were also expressed as an index relative to P1075. The index was calculated by dividing the $ED_{50}$ for P1075 by the $ED_{50}$ for the test agonist in a given tissue. Each tissue was used for only one test agonist, and the indices obtained from each tissue were averaged to provide an average index of potency. These data are shown in Table 2.

TABLE 2

Functional Potassium Channel Opening Activity in Isolated Bladder Strips

| | Landrace Pig Bladder | | |
|---|---|---|---|
| Example # | Efficacy (% P1075) | $pD_2$ | Index |
| 1 | 96 | 6.47 | 0.26 |
| 15 | 100 | 6.67 | 0.21 |
| 16 | 95 | 6.34 | 0.28 |

As shown by the data in Tables 1 and 2, the compounds of this invention reduce stimulated contractions of the bladder and therefore may have utility in the treatment of diseases prevented by or ameliorated with potassium channel openers.

Compounds of the present invention may exist as stereoisomers wherein, asymmetric or chiral centers are present. These stereoisomers are "R" or "S" depending on the configuration of substituents around the chiral carbon atom. The terms "R" and "S" used herein are configurations as defined in IUPAC 1974 Recommendations for Section E, Fundamental Stereochemistry, Pure Appl. Chem., 1976, 45: 13–30. In particular, the stereochemistry at the point of attachment of $R^1$, as shown in formula I–IV, may independently be either (R) or (S), unless specifically noted otherwise. The present invention contemplates various stereoisomers and mixtures thereof and are specifically included within the scope of this invention. Stereoisomers include enantiomers and diastereomers, and mixtures of enantiomers or diastereomers. Individual stereoisomers of compounds of the present invention may be prepared synthetically from commercially available starting materials which contain asymmetric or chiral centers or by preparation of racemic mixtures followed by resolution well-known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary or (2) direct separation of the mixture of optical enantiomers on chiral chromatographic columns.

The term "pharmaceutically acceptable carrier," as used herein, means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The present invention provides pharmaceutical compositions which comprise compounds of the present invention formulated together with one or more non-toxic pharmaceutically acceptable carriers. The pharmaceutical compositions can be formulated for oral administration in solid or liquid form, for parenteral injection or for rectal administration.

Further included within the scope of the present invention are pharmaceutical compositions comprising one or more of the compounds of formula I–IV prepared and formulated in combination with one or more non-toxic pharmaceutically acceptable compositions. The pharmaceutical compositions can be formulated for oral administration in solid or liquid form, for parenteral injection or for rectal administration.

The pharmaceutical compositions of this invention can be administered to humans and other mammals orally, rectally, parenterally, intracisternally, intravaginally, intraperitoneally, topically (as by powders, ointments or drops), bucally or as an oral or nasal spray. The term "parenterally," as used herein, refers to modes of administration which include intravenous, intramuscular, intraperitoneal, intrasternal, subcutaneous, intraarticular injection and infusion.

Pharmaceutical compositions of this invention for parenteral injection comprise pharmaceutically acceptable sterile aqueous or nonaqueous solutions, dispersions, suspensions or emulsions and sterile powders for reconstitution into sterile injectable solutions or dispersions. Examples of suitable aqueous and nonaqueous carriers, diluents, solvents or vehicles include water, ethanol, polyols (propylene glycol, polyethylene glycol, glycerol, and the like), suitable mixtures thereof, vegetable oils (such as olive oil) and injectable organic esters such as ethyl oleate. Proper fluidity may be maintained, for example, by the use of a coating such as lecithin, by the maintenance of the required particle size in the case of dispersions, and by the use of surfactants.

These compositions may also contain adjuvants such as preservative agents, wetting agents, emulsifying agents, and dispersing agents. Prevention of the action of microorganisms may be ensured by various antibacterial and antifungal agents, for example, parabens, chlorobutanol, phenol, sorbic acid, and the like. It may also be desirable to include isotonic agents, for example, sugars, sodium chloride and the like. Prolonged absorption of the injectable pharmaceutical form may be brought about by the use of agents delaying absorption, for example, aluminum monostearate and gelatin.

In some cases, in order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Suspensions, in addition to the active compounds, may contain suspending agents, as, for example, ethoxylated isostearyl alcohols, polyoxyethylene sorbitol and sorbitan esters, microcrystalline cellulose, aluminum metahydroxide, bentonite, agar-agar, tragacanth, and mixtures thereof.

If desired, and for more effective distribution, the compounds of the present invention can be incorporated into slow-release or targeted-delivery systems such as polymer matrices, liposomes, and microspheres. They may be sterilized, for example, by filtration through a bacteria-retaining filter or by incorporation of sterilizing agents in the form of sterile solid compositions, which may be dissolved in sterile water or some other sterile injectable medium immediately before use.

The active compounds can also be in micro-encapsulated form, if appropriate, with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound can be admixed with at least one inert diluent such as sucrose, lactose, or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of such composition that they release the active ingredient(s) only, or preferentially, in a certain part of the intestinal tract in a delayed manner. Examples of embedding compositions which can be used include polymeric substances and waxes.

Injectable depot forms are made by forming microencapsulated matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides) Depot injectable formulations are also prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic, parenterally acceptable diluent or solvent such as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid; b) binders such as carboxymethylcellulose, alginates, gelatin, polyvinylpyrrolidinone, sucrose, and acacia; c) humectants such as glycerol; d) disintegrating agents such as agar-agar, calcium carbonate, potato or tapioca starch, alginic acid, certain silicates, and sodium carbonate; e) solution retarding agents such as paraffin; f) absorption accelerators such as quaternary ammonium compounds; g) wetting agents such as cetyl alcohol and glycerol monostearate;) absorbents such as kaolin and bentonite clay; and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract in a delayed manner. Examples of embedding compositions which can be used include polymeric substances and waxes.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfiiryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Compounds of the present invention may also be administered in the form of liposomes. As is known in the art, liposomes are generally derived from phospholipids or other lipid substances. Liposomes are formed by mono- or multilamellar hydrated liquid crystals that are dispersed in an aqueous medium. Any non-toxic, physiologically acceptable and metabolizable lipid capable of forming liposomes may be used. The present compositions in liposome form may contain, in addition to the compounds of the present invention, stabilizers, preservatives, excipients, and the like. The preferred lipids are the natural and synthetic phospholipids and phosphatidylcholines (lecithins) used separately or together.

Methods to form liposomes are known in the art. See, for example, Prescott, Ed., Methods in Cell Biology, Volume XIV, Academic Press, New York, N.Y., (1976), p 33 et seq.

The terms "pharmaceutically acceptable salts, esters and amides," as used herein, refer to carboxylate salts, amino acid addition salts, zwitterions, esters and amides of compounds of formula I–IV which are, within the scope of sound medical judgement, suitable for use in contact with the tissues of humans and lower animals without undue toxicity, irritation, allergic response, and the like, are commensurate with a reasonable benefit/risk ratio, and are effective for their intended use.

The compounds of the present invention can be used in the form of pharmaceutically acceptable salts derived from inorganic or organic acids. By "pharmaceutically acceptable salt" is meant those salts which are, within the scope of sound medical judgement, suitable for use in contact with the tissues of humans and lower animals without undue toxicity, irritation, allergic response and the like and are commensurate with a reasonable benefit/risk ratio. Pharmaceutically acceptable salts are well-known in the art. For example, S. M. Berge et al. describe pharmaceutically acceptable salts in detail in J. Pharmaceutical Sciences, 1977, 66: 1 et seq. The salts can be prepared in situ during the final isolation and purification of the compounds of the invention or separately by reacting a free base finction with a suitable organic acid. Representative acid addition salts include, but are not limited to acetate, adipate, alginate, citrate, aspartate, benzoate, benzenesulfonate, bisulfate, butyrate, camphorate, camphorsufonate, digluconate, glycerophosphate, hemisulfate, heptanoate, hexanoate, fumarate, hydrochloride, hydrobromide, hydroiodide, 2-hydroxyethansulfonate (isethionate), lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quaternized with such agents as lower alkyl halides such as methyl, ethyl, propyl, and butyl chlorides, bromides and iodides; dialkyl sulfates like dimethyl, diethyl, dibutyl and diamyl sulfates; long chain halides such as decyl, lauryl, myristyl and stearyl chlorides, bromides and iodides; arylalkyl halides like benzyl and phenethyl bromides and others. Water or oil-soluble or dispersible products are thereby obtained. Examples of acids which can be employed to form pharmaceutically acceptable acid addition salts include such inorganic acids as hydrochloric acid, hydrobromic acid, sulphuric acid and phosphoric acid and such organic acids as oxalic acid, maleic acid, succinic acid and citric acid.

Basic addition salts can be prepared in situ during the final isolation and purification of compounds of this invention by reacting a carboxylic acid-containing moiety with a suitable base such as the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as lithium, sodium, potassium, calcium, magnesium and aluminum salts and the like and nontoxic quaternary ammonia and amine cations including ammonium, tetramethylammonium, tetraethylammonium, methylamine, dimethylamine, trimethylamine, triethylamine, diethylamine, ethylamine and the like. Other representative organic amines useful for the formation of base addition salts include ethylenediamine, ethanolamine, diethanolamine, piperidine, piperazine and the like. Preferred salts of the compounds of the invention include phosphate, tris and acetate.

The term "pharmaceutically acceptable ester," as used herein, refers to esters of compounds of the present invention which hydrolyze in vivo and include those that break down readily in the human body to leave the parent compound or a salt thereof. Examples of pharmaceutically acceptable, non-toxic esters of the present invention include $C_1$-to-$C_6$ alkyl esters and $C_5$-to-$C_7$ cycloalkyl esters, although $C_1$-to-$C_4$ alkyl esters are preferred. Esters of the compounds of formula I–IV may be prepared according to conventional methods. For example, 9-(3,4-dichlorophenyl)-3-(4-carboxyphenyl)-5,6,7,9-tetrahydropyrazolo[5,1-b]quinazolin-8(4H)-one can be treated with an acid, such as HCl, in an alcoholic solvent, such as methanol, to provide the ester 9-(3,4-dichlorophenyl)-3-(4- methoxycarbonylphenyl)-5,6,7,9-tetrahydropyrazolo[5,1-b]quinazolin-8(4H)-one.

The term "pharmaceutically acceptable amide," as used herein, refers to non-toxic amides of the present invention derived from ammonia, primary $C_1$-to-$C_6$ alkyl amines and secondary $C_1$-to-$C_6$ dialkyl amines. In the case of secondary amines, the amine may also be in the form of a 5- or 6-membered heterocycle containing one nitrogen atom. Amides derived from ammonia, $C_1$-to-$C_3$ alkyl primary amides and $C_1$-to-$C_2$ dialkyl secondary amides are preferred. Amides of the compounds of formula I–IV may be prepared according to conventional methods. For example, 9-(3,4-dichlorophenyl)-3-(4-carboxyphenyl)-5,6,7,9-tetrahydropyrazolo[5,1-b]quinazolin-8(4H)-one can be treated with a chloroformate, such as isobutylchloroformate, in an organic solvent, such as tetrahydrofuran or methylene chloride at a temperature of about 0° C. to ambient temperature, to provide an intermediate anhydride which can then be treated with an amine, such as dimethylamine, to provide 9-(3,4-dichlorophenyl)-3-(4-dimethylaminocarbonylphenyl)-5,6,7,9-tetrahydropyrazolo[5,1-b]quinazolin-8(4H)-one. It is further intended that amides of the present invention include amino acid and peptide derivatives of the compounds of formula I, as well.

The term "pharmaceutically acceptable prodrug" or "prodrug," as used herein, represents those prodrugs of the compounds of the present invention which are, within the scope of sound medical judgement, suitable for use in contact with the tissues of humans and lower animals without undue toxicity, irritation, allergic response, and the like, commensurate with a reasonable benefit/risk ratio, and effective for their intended use. Prodrugs of the present invention may be rapidly transformed in vivo to the parent compound of the above formula, for example, by hydrolysis in blood. A thorough discussion is provided in T. Hiquchi and V. Stella, Pro-drugs as Novel Delivery Systems, V. 14 of the A.C.S. Symposium Series, and in Edward B. Roche, ed., Bioreversible Carriers in Drug Design, American Pharmaceutical Association and Pergamon Press (1987), hereby incorporated by reference.

Dosage forms for topical administration of a compound of this invention include powders, sprays, ointments and inhalants. The active compound is mixed under sterile conditions with a pharmaceutically acceptable carrier and any needed preservatives, buffers or propellants which can be required. Opthalmic formulations, eye ointments, powders and solutions are also contemplated as being within the scope of this invention.

Actual dosage levels of active ingredients in the pharmaceutical compositions of this invention can be varied so as to obtain an amount of the active compound(s) which is effective to achieve the desired therapeutic response for a particular patient, compositions and mode of administration. The selected dosage level will depend upon the activity of the particular compound, the route of administration, the severity of the condition being treated and the condition and prior medical history of the patient being treated. However, it is within the skill of the art to start doses of the compound at levels lower than required for to achieve the desired therapeutic effect and to gradually increase the dosage until the desired effect is achieved.

The present invention contemplates pharmaceutically active compounds either chemically synthesized or formed by in vivo biotransformation to compounds of formula I–IV.

The compounds of the invention, including but not limited to those specified in the examples, possess potassium channel opening activity in mammals (especially humans). As potassium channel openers, the compounds of the present invention are useful for the treatment and prevention of diseases such as asthma, epilepsy, hypertension, Raynaud's syndrome, male sexual dysfunction, female sexual dysfimction, migraine, pain, eating disorders, urinary incontinence, functional bowel disorders, neurodegeneration and stroke.

The ability of the compounds of the invention to treat asthma, epilepsy, hypertension, Raynaud's syndrome, male sexual dysfunction, female sexual dysfunction, migraine, pain, eating disorders, urinary incontinence, functional bowel disorders, neurodegeneration and stroke can be demonstrated according to the methods described in (D. E. Nurse et al., Br. J. Urol., v. 68 pp. 27–31 (1991); B. B. Howe et al., J. Pharmacol. Exp. Ther., v. 274 pp. 884–890 (1995); K. Lawson, Pharmacol. Ther., v. 70 pp. 39–63 (1996); D. R. Gehlert, et al., Neuro-Psychopharmacol & Biol. Psychiat., v. 18 pp. 1093–1102 (1994); M. Gopalakrishnan et al., Drug Development Research, v. 28 pp. 95–127 (1993); J. E. Freedman et al., The Neuroscientist, v. 2 pp. 145–152 (1996); D. Spanswick et al., Nature, v. 390 pp. 521–25 (Dec. 4, 1997)).

Aqueous liquid compositions of the present invention are particularly useful for the treatment and prevention of asthma, epilepsy, hypertension, Raynaud's syndrome, male sexual dysfunction, female sexual dysfunction, migraine, pain, eating disorders, urinary incontinence, functional bowel disorders, neurodegeneration and stroke.

When used in the above or other treatments, a therapeutically effective amount of one of the compounds of the present invention can be employed in pure form or, where such forms exist, in pharmaceutically acceptable salt, ester, amide or prodrug form. Alternatively, the compound can be administered as a pharmaceutical composition containing the compound of interest in combination with one or more pharmaceutically acceptable excipients. The phrase "therapeutically effective amount" of the compound of the invention means a sufficient amount of the compound to treat disorders, at a reasonable benefit/risk ratio applicable to any medical treatment. It will be understood, however, that the total daily usage of the compounds and compositions of the present invention will be decided by the attending physician within the scope of sound medical judgement. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts. For example, it is well within the skill of the art to start doses of the compound at levels lower than required to achieve the desired therapeutic effect and to gradually increase the dosage until the desired effect is achieved.

The total daily dose of the compounds of this invention administered to a human or lower animal may range from about 0.003 to about 10 mg/kg/day. For purposes of oral administration, more preferable doses can be in the range of from about 0.01 to about 5 mg/kg/day. If desired, the effective daily dose can be divided into multiple doses for purposes of administration; consequently, single dose compositions may contain such amounts or submultiples thereof to make up the daily dose.

We claim:

1. A compound having formula I:

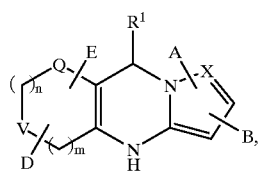

I or a pharmaceutically acceptable salt thereof wherein, n is an integer 0–1;

m is an integer 1–2;

provided that when m is 2, n is 0;

$R^1$ is selected from the group consisting of aryl and heterocycle;

Q is selected from the group consisting of C(O), S(O), and $S((O)_2$;

V is selected from the group consisting of $C(R^6)(R^7)$, O, S, and $NR^2$, wherein $R^2$ is selected from the group consisting of hydrogen, alkenyl, alkoxy, alkoxyalkoxy, alkoxyalkyl, alkyl, alkynyl, aryl, arylalkoxy, arylalkenyl, arylalkyl, cyano, cycloalkyl, cycloalkylalkyl, haloalkoxy, haloalkyl, heterocycle, heterocyclealkyl, hydroxy, hydroxyalkyl, —$NR^4R^5$, and $(NR^4R^5)$alkyl wherein $R^4$ and $R^5$ are independently selected from the group consisting of hydrogen and lower alkyl;

$R^6$ and $R^7$ are independently selected from the group consisting of hydrogen, alkenyl, alkoxy, alkoxyalkoxy, alkoxyalkyl, alkyl, alkylthio, alkynyl, aryl, arylalkoxy, arylalkenyl, arylalkyl, carboxy, cyano, cycloalkyl, cycloalkylalkyl, haloalkoxy, haloalkyl, halogen, heterocycle, heterocyclealkyl, hydroxy, hydroxyalkyl, oxo, —$NR^4R^5$, and $(NR^4R^5)$alkyl;

X is selected from the group consisting of N and $CR^3$, wherein $R^3$ is selected from the group consisting of hydrogen, alkenyl, alkoxy, alkoxyalkoxy, alkoxyalkyl, alkyl, alkylthio, alkynyl, aryl, arylalkoxy, arylalkenyl, arylalkyl, carboxy, cyano, cycloalkyl, cycloalkylalkyl, haloalkoxy, haloalkyl, halogen, heterocycle, heterocyclealkyl, hydroxy, hydroxyalkyl, —$NR^4R^5$, and $(NR^4R^5)$alkyl;

A and B are independently selected from the group consisting of hydrogen, alkenyl, alkoxy, alkoxyalkoxy, alkoxyalkyl, alkyl, alkylthio, alkynyl, aryl, arylalkoxy, arylalkenyl, arylalkyl, carboxy, cyano, cycloalkyl, cycloalkylalkyl, haloalkoxy, haloalkyl, halogen, heterocycle, heterocyclealkyl, hydroxy, hydroxyalkyl, —$NR^4R^5$, and $(NR^4R^5)$alkyl; and D and E are independently selected from the group consisting of hydrogen, alkenyl, alkoxy, alkoxyalkoxy, alkoxyalkyl, alkyl, alkylthio, alkynyl, aryl, arylalkoxy, arylalkenyl, arylalkyl, carboxy, cyano, cycloalkyl, cycloalkylalkyl, haloalkoxy, haloalkyl, halogen, heterocycle, heterocyclealkyl, hydroxy, hydroxyalkyl, oxo, —$NR^4R^5$, and $(NR^4R^5)$alkyl.

2. A compound according to claim 1 wherein, $R^1$ is aryl;

X is $CR^3$; and $R^3$ is hydrogen.

3. A compound according to claim 1 wherein, $R^1$ is heterocycle;

X is $CR^3$; and $R^3$ is hydrogen.

4. A compound according to claim 1 of formula II:

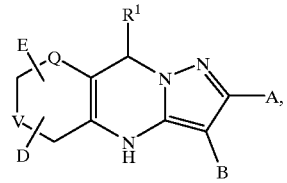

II or a pharmaceutically acceptable salt thereof $R^1$ is selected from aryl and heterocycle;

Q is selected from C(O), S(O), and $S(O)_2$;

V is selected from $C(R^6)(R^7)$, O, S, and $NR^2$, wherein $R^2$ is selected from hydrogen, alkenyl, alkoxy, alkoxyalkoxy, alkoxyalkyl, alkyl, alkynyl, aryl, arylalkoxy, arylalkenyl, arylalkyl, cyano, cycloalkyl, cycloalkylalkyl, haloalkoxy, haloalkyl, heterocycle, heterocycloalkyl, hydroxy, hydroxyalkyl, —$NR^4R^5$ and $(NR^4R^5)$alkyl wherein $R^4$ and $R^5$ are independently selected from hydrogen and lower alkyl;

$R^6$ and $R^7$ are independently selected from hydrogen, alkenyl, alkoxy, alkoxyalkoxy, alkoxyalkyl, alkyl, alkylthio, alkynyl, aryl, arylalkoxy, arylalkenyl, arylalkyl, carboxy, cyano, cycloalkyl, cycloalkylalkyl, haloalkoxy, haloalkyl, halogen, heterocycle, heterocycloalkyl, hydroxy, hydroxyalkyl, oxo, —$NR^4R^5$, and $(^4R^5)$alkyl;

A and B are independently selected from hydrogen, alkenyl, alkoxy, alkoxyalkoxy, alkoxyalkyl, alkyl, alkylthio, alkynyl, aryl, arylalkoxy, arylalkenyl, arylalkyl, carboxy, cyano, cycloalkyl, cycloalkylalkyl, haloalkoxy, haloalkyl, halogen, heterocycle, heterocyclealkyl, hydroxy, hydroxyalkyl, —NR$^4$R$^5$, and (NR$^4$R$^5$)alkyl; and D and E are independently selected from hydrogen, alkenyl, alkoxy, alkoxyalkoxy, alkoxyalkyl, alkyl, alkylthio, alkynyl, aryl, arylalkoxy, arylalkenyl, arylalkyl, carboxy, cyano, cycloalkyl, cycloalkylalkyl, haloalkoxy, haloalkyl, halogen, heterocycle, heterocyclealkyl, hydroxy, hydroxyalkyl, oxo, —NR$^4$R$^5$, and (NR$^4$R$^5$)alkyl.

5. A compound according to claim 4 wherein,
R$^1$ is heterocycle; and
Q is C(O).

6. A compound according to claim 4 wherein,
R$^1$ is heterocycle; and
Q is S(O).

7. A compound according to claim 4 wherein,
R$^1$ is heterocycle; and
Q is S((O)$_2$).

8. A compound according to claim 4 wherein,
R$^1$ is heterocycle;
Q is C(O); and
V is S.

9. A compound according to claim 4 wherein,
R$^1$ is heterocycle;
Q is C(O);
V is S;
A is hydrogen;
B is hydrogen;
D is hydrogen; and
E is hydrogen.

10. A compound according to claim 4 wherein,
R$^1$ is heterocycle;
Q is C(O); and
V is CH$_2$.

11. A compound according to claim 4 wherein,
R$^1$ is heterocycle;
Q is C(O);
V is CH$_2$;
D is alkyl; and
E is alkyl.

12. A compound according to claim 4 wherein,
R$^1$ is heterocycle;
Q is C(O);
V is CH$_2$;
D is alkyl;
E is alkyl;
A is hydrogen; and
B is hydrogen.

13. A compound according to claim 4 wherein,
R$^1$ is heterocycle;
Q is C(O);
V is CH$_2$;
A is hydrogen;
B is hydrogen;
D is hydrogen; and
E is hydrogen.

14. A compound according to claim 4 wherein,
R$^1$ is heterocycle;
Q is S((O)$_2$); and
V is CH$_2$.

15. A compound according to claim 4 wherein,
R$^1$ is heterocycle;
Q is S((O)$_2$);
V is CH$_2$;
A is hydrogen;
B is hydrogen;
D is hydrogen; and
E is hydrogen.

16. A compound according to claim 4 wherein,
R$^1$ is aryl; and
Q is C(O).

17. A compound according to claim 4 wherein,
R$^1$ is aryl;
Q is C(O); and
V is S.

18. A compound according to claim 4 wherein,
R$^1$ is aryl;
Q is C(O);
V is S;
A is hydrogen;
B is hydrogen;
D is hydrogen; and
E is hydrogen.

19. A compound according to claim 18 that is 9-(3-bromo-4-fluorophenyl)-5,9-dihydro-4H-pyrazolo[1,5-a]thiopyrano[3,4-d]pyrimidin-8(7H)-one.

20. A compound according to claim 4 wherein,
R$^1$ is aryl;
Q is C(O); and
V is CH$_2$.

21. A compound according to claim 4 wherein,
R$^1$ is aryl;
Q is C(O);
V is CH$_2$;
D is alkyl; and
E is alkyl.

22. A compound according to claim 4 wherein,
R$^1$ is aryl;
Q is C(O);
V is CH$_2$;
D is alkyl;
E is alkyl;
A is hydrogen; and
B is hydrogen.

23. A compound according to claim 4 wherein,
R$^1$ is aryl;
Q is C(O);
V is CH$_2$; and
B is aryl.

24. A compound according to claim 4 wherein,
R$^1$ is aryl;
Q is C(O);
V is CH$_2$;
B is aryl;
A is hydrogen;
D is hydrogen; and E is hydrogen.

25. A compound according to claim 4 wherein,
$R^1$ is aryl;
Q is C(O);
V is $CH_2$; and
B is heterocycle.

26. A compound according to claim 4 wherein,
$R^1$ is aryl;
Q is C(O);
V is $CH_2$;
B is heterocycle;
A is hydrogen;
D is hydrogen; and
E is hydrogen.

27. A compound according to claim 4 wherein,
$R^1$ is aryl;
Q is C(O);
V is $CH_2$; and
B is halogen.

28. A compound according to claim 4 wherein,
$R^1$ is aryl;
Q is C(O);
V is $CH_2$;
B is halogen;
A is hydrogen;
D is hydrogen; and
E is hydrogen.

29. A compound according to claim 4 wherein,
$R^1$ is aryl;
Q is C(O);
V is $CH_2$;
A is hydrogen;
B is hydrogen;
D is hydrogen; and
E is hydrogen.

30. A compound according to claim 29 that is selected from the group consisting of 9-(3-bromo-4-fluorophenyl)-5,6,7,9-tetrahydropyrazolo[5,1-b]quinazolin-8(4H) one,
9-(1-naphthyl)-5,6,7,9-tetrahydropyrazolo[5,1-b]quinazolin-8(4H)-one,
9-(2-naphthyl)-5,6,7,9-tetrahydropyrazolo[5,1-b]quinazolin-8(4H)-one,
9-(3,4-dibromophenyl)-5,6,7,9-tetrahydropyrazolo[5,1-b]quinazolin-8(4H)-one,
9-(3,4-dichlorophenyl)-5,6,7,9-tetrahydropyrazolo[5,1-b]quinazolin-8(4H)-one,
9-(3-bromophenyl)-5,6,7,9-tetrahydropyrazolo[5,1-b]quinazolin-8(4H)-one,
9-(3-chlorophenyl)-5,6,7,9-tetrahydropyrazolo[5,1-b]quinazolin-8(4H)-one,
9-[4-chloro-3-(trifluoromethyl)phenyl]-5,6,7,9-tetrahydropyrazolo[5,1-b]quinazolin-8(4H)-one,
9-[4-fluoro-3-(trifluoromethyl)phenyl]-5,6,7,9-tetrahydropyrazolo[5,1-b]quinazolin-8(4H)-one,
9-[3-(trifluoromethoxy)phenyl]-5,6,7,9-tetrahydropyrazolo[5,1-b]quinazolin-8(4H)-one,
9-(3-cyanophenyl)-5,6,7,9-tetrahydropyrazolo[5,1-b]quinazolin-8(4H)-one,
9-(3-methylphenyl)-5,6,7,9-tetrahydropyrazolo[5,1-b]quinazolin-8(4H)-one,
(−) 9-(3-bromo-4-fluorophenyl)-5,6,7,9-tetrahydropyrazolo[5,1-b]quinazolin-8(4H)-one, and
(+) 9-(3-bromo-4-fluorophenyl)-5,6,7,9-tetrahydropyrazolo[5,1-b]quinazolin-8(4H)-one.

31. A compound according to claim 4 wherein,
$R^1$ is aryl; and
Q is S(O).

32. A compound according to claim 4 wherein,
$R^1$ is aryl; and
Q is $S(O)_2$.

33. A compound according to claim 4 wherein,
$R^1$ is aryl;
Q is $S((O)_2$; and
V is $CH_2$.

34. A compound according to claim 4 wherein,
$R^1$ is aryl;
Q is $S(O)_2$;
V is $CH_2$;
A is hydrogen;
B is hydrogen;
D is hydrogen; and
E is hydrogen.

35. A compound according to claim 34 that is 9-(3-bromo-4-fluorophenyl)-5,6,7,9-tetrahydro-4H-pyrazolo[1,5-a]thiopyrano[3,2-d]pyrimidine 8,8-dioxide.

36. A compound according to claim 1 of formula III:

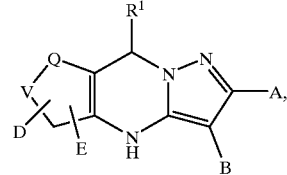

III or a pharmaceutically acceptable salt thereof
$R^1$ is selected from aryl and heterocycle;
Q is selected from C(O), S(O), and $S(O)_2$;
V is selected from $C(R^6)(R^7)$, O, S, and $NR^2$, wherein $R^2$ is selected from hydrogen, alkenyl, alkoxy, alkoxyalkoxy, alkoxyalkyl, alkyl, alkynyl, aryl, arylalkoxy, arylalkenyl, arylalkyl, cyano, cycloalkyl, cycloalkylalkyl, haloalkoxy, haloalkyl, heterocycle, heterocyclealkyl, hydroxy, hydroxyalkyl, —$NR^4R^5$, and $(NR^4R^5)$alkyl wherein $R^4$ and $R^5$ are independently selected from hydrogen and lower alkyl;

$R^6$ and $R^7$ are independently selected from hydrogen, alkenyl, alkoxy, alkoxyalkoxy, alkoxyalkyl, alkyl, alkylthio, alkynyl, aryl, arylalkoxy, arylalkenyl, arylalkl, carboxy, cyano, cycloalkyl, cycloalkylalkyl, haloalkoxy, haloalkyl, halogen, heterocycle, heterocyclealkyl, hydroxy, hydroxyalkyl, oxo, —$NR^4R^5$, and $(NR^4R^5)$alkyl;

A and B are independently selected from hydrogen, alkenyl, alkoxy, alkoxyalkoxy, alkoxyalkyl, alkyl, alkylthio, alkynyl, aryl, arylalkoxy, arylalkenyl, arylalkyl, carboxy, cyano, cycloalkyl, cycloalkylalkyl, haloalkoxy, haloalkyl, halogen, heterocycle, heterocycloalkyl, hydroxy, hydroxyalkyl, —$NR^4R^5$, and $(NR^4R^5)$alkyl, and D and E are independently selected from hydrogen, alkenyl, alkoxy, alkoxyalkoxy, alkoxyalkyl, alkyl, alkylthio, alkynyl, aryl, arylalkoxy, arylalkenyl, arylalkyl, carboxy, cyano, cycloalkyl, cycloalkylalkyl, haloalkoxy, haloalkyl, halogen, heterocycle, heterocyclealkyl, hydroxy, hydroxyalkyl, oxo, —NR$^4$R$^5$, and (NR$^4$R$^5$)alkyl.

37. A compound according to claim 36 wherein,
R$^1$ is heterocycle; and
Q is C(O).

38. A compound according to claim 36 wherein,
R$^1$ is heterocycle; and
Q is S(O).

39. A compound according to claim 36 wherein,
R$^1$ is heterocycle; and
Q is S((O)$_2$.

40. A compound according to claim 36 wherein,
R$^1$ is aryl; and
Q is C(O).

41. A compound according to claim 36 wherein,
R$^1$ is aryl;
Q is C(O); and
V is O.

42. A compound according to claim 36 wherein,
R$^1$ is aryl;
Q is C(O);
A is hydrogen;
B is hydrogen;
D is hydrogen; and
E is hydrogen.

43. A compound according to claim 42 that is 8-(3-bromo-4-fluorophenyl)-5,8-dihydro-4H,7H-furo[3,4-d]pyrazolo[1,5-a]pyrimidin-7-one.

44. A compound according to claim 36 wherein,
R$^1$ is aryl; and
Q is S(O).

45. A compound according to claim 36 wherein,
R$^1$ is aryl; and
Q is S((O)$_2$.

46. A compound according to claim 1 of formula IV:

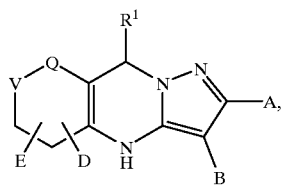

IV or a pharmaceutically acceptable salt thereof wherein,
R$^1$ is selected from aryl and heterocycle;
Q is selected from C(O), S(O), and S(O)$_2$;
V is selected from C(R$^6$)(R$^7$) O, S, and NR$^2$ wherein R$^2$ is selected from hydrogen, alkenyl alkoxy, alkoxyalkoxy, alkoxyalkyl, alkyl, alkynyl, aryl, arylalkoxy, arylalkenyl, arylalkyl, cyano, cycloalkyl, cycloalkylalkyl, haloalkoxy, haloalkyl, heterocycle, heterocyclealkyl, hydroxy, hydroxyalkyl, —NR$^4$R$^5$, and (NR$^4$R$^5$)alkyl wherein R$^4$ and R$^5$ are independently selected from hydrogen and lower alkyl;
R$^6$ and R$^7$ are independently selected from hydrogen, alkenyl, alkoxy, alkoxyalkoxy, alkoxyalkyl, alkyl, alkylthio, alkynyl, aryl, arylalkoxy, arylalkenyl arylalkyl, carboxyy, cyano, cycloalkyl, cycloalkylalkyl, haloalkoxy, haloalkyl, halogen, heterocycle, heterocyclealkyl, hydroxy, hydroxyalkyl, oxo, —NR$^4$R$^5$, and (NR$^4$R$^5$)alkyl;

A and B are independently selected from hydrogen, alkenyl, alkoxy, alkoxyalkoxy, alkoxyalkyl, alkyl, alkylthio, alkynyl, aryl, arylalkoxy, arylalkenyl, arlalkyl, carboxy, cyano, cycloalkyl, cycloalkylalkyl, haloalkoxy, haloalkyl, halogen, heterocycle, heterocycloalkyl, hydroxy, hydroxyalkyl, —NR$^4$R$^5$, and (NR$^4$R$^5$)alkyl; and D and E are independently selected from hydrogen, alkenyl, alkoxy, alkoxyalkoxy, alkoxyalkyl, alkyl, alkylthio, alkynyl aryl, arylalkoxy, arylalkenyl, arylalkyl, carboxy, cyano, cycloalkyl, cycloalkylalkyl, haloalkoxy, haloalkyl, halogen, heterocycle, heterocyclealkyl, hydroxy, hydroxyalkyl, oxo, —NR$^4$R$^5$, and (NR$^4$R$^5$)alkyl.

47. A compound according to claim 46 wherein,
R$^1$ is heterocycle; and
Q is C(O).

48. A compound according to claim 46 wherein,
R$^1$ is heterocycle; and
Q is S(O).

49. A compound according to claim 46 wherein,
R$^1$ is heterocycle; and
Q is S((O)$_2$.

50. A compound according to claim 46 wherein,
R$^1$ is aryl; and
Q is C(O).

51. A compound according to claim 46 wherein,
R$^1$ is aryl; and
Q is S(O).

52. A compound according to claim 46 wherein,
R$^1$ is aryl; and
Q is S((O)$_2$.

53. A pharmaceutical composition comprising a therapeutically effective amount of a compound of claim 1 in combination with a pharmaceutically acceptable carrier.

54. A method of treating a disease selected from the group consisting of asthma, epilepsy, hypertension, Raynaud's syndrome, migraine, pain, eating disorders, functional bowel disorders, neurodegeneration, and stroke comprising administering to a mammal a therapeutically effective amount of a compound of claim 1.

55. A method of treating urinary incontinence.

56. A method of treating selected from the group consisting of male erectile dysfunction and premature ejaculation comprising administering to a mammal a therapeutically effective amount of a compound of claim 1.

57. A method of treating selected from the group consisting of female anorgasmia, clitoral erectile insufficiency, vaginal engorgement, dyspareunia, and vaginismus comprising administering to a mammal a therapeuticaly effective amount of a compound of claim 1.

* * * * *